United States Patent
Mizera et al.

(10) Patent No.: US 12,257,168 B2
(45) Date of Patent: Mar. 25, 2025

(54) DEVICE FOR SUPPORTING AT LEAST ONE ARM OF A USER

(71) Applicant: OTTOBOCK SE & CO. KGAA, Duderstadt (DE)

(72) Inventors: Oliver Mizera, Göttingen (DE); Annedore Kurzweg, Göttingen (DE); Lüder Mosler, Duderstadt (DE); Jonas Bornmann, Duderstadt (DE); Samantha Fox, Waitsfield, VT (US); Benjamin Schirrmeister, Göttingen (DE)

(73) Assignee: Ottobock SE & Co. KGAA, Duderstadt (DE)

( * ) Notice: Subject to any disclaimer, the term of this patent is extended or adjusted under 35 U.S.C. 154(b) by 925 days.

(21) Appl. No.: 16/492,420

(22) PCT Filed: Jun. 6, 2018

(86) PCT No.: PCT/EP2018/064910
§ 371 (c)(1),
(2) Date: Sep. 9, 2019

(87) PCT Pub. No.: WO2018/224555
PCT Pub. Date: Dec. 13, 2018

(65) Prior Publication Data
US 2020/0038219 A1    Feb. 6, 2020

(30) Foreign Application Priority Data
Jun. 6, 2017  (DE) ............... 10 2017 112 436.5

(51) Int. Cl.
*A61F 5/01*    (2006.01)
*A61H 1/00*    (2006.01)
(Continued)

(52) U.S. Cl.
CPC ............ *A61F 5/0118* (2013.01); *A61F 5/013* (2013.01); *A61H 1/0274* (2013.01);
(Continued)

(58) Field of Classification Search
USPC .......................................................... 414/9
See application file for complete search history.

(56) References Cited

U.S. PATENT DOCUMENTS

| 5,868,694 A | 2/1999 | Marlow et al. |
| 9,427,865 B2 | 8/2016 | Doyle |

(Continued)

FOREIGN PATENT DOCUMENTS

| CN | 105050774 A | 11/2015 |
| DE | 102009046068 A1 | 5/2011 |

(Continued)

*Primary Examiner* — David H Willse
(74) *Attorney, Agent, or Firm* — WCF IP

(57) ABSTRACT

The invention relates to a device for supporting at least one arm 4 of a user 2. The device has at least one arm support element 6 with an arm shell 10 for placing on the arm 4, at least one passive actuator 26 that is configured to apply a force on the at least one arm support element 6, and at least one counter bearing 14 for the force to be applied. The counter bearing has at least one counter bearing element 16 and at least one force transmission element 18 that is configured to transmit a counter-force to the counter bearing element 16. The freedom of movement of the spine of the user 2 is not restricted by the device. More particularly an inclination is possible and/or a freedom of movement of the arm 4 is not restricted by the device.

34 Claims, 22 Drawing Sheets

(51) Int. Cl.
   *A61H 1/02*     (2006.01)
   *A61H 3/00*     (2006.01)
   *B25J 9/00*     (2006.01)
   *B25J 9/10*     (2006.01)

(52) U.S. Cl.
   CPC ............ *A61H 1/0281* (2013.01); *A61H 3/00* (2013.01); *B25J 9/0006* (2013.01); *B25J 9/0009* (2013.01); *B25J 9/108* (2013.01); *A61F 2005/0134* (2013.01); *A61F 2005/0155* (2013.01); *A61F 2005/0179* (2013.01); *A61H 2001/0203* (2013.01); *A61H 2003/007* (2013.01); *A61H 2201/1638* (2013.01); *A61H 2201/165* (2013.01); *A61H 2201/1673* (2013.01); *A61H 2201/168* (2013.01)

(56) References Cited

U.S. PATENT DOCUMENTS

| | | | |
|---|---|---|---|
| 10,857,021 B2 * | 12/2020 | Mizera | ............... A61H 1/0274 |
| 2012/0184880 A1 | 7/2012 | Doyle | |
| 2014/0033391 A1 | 2/2014 | Doyle | |
| 2014/0276308 A1 | 9/2014 | DiAngelo et al. | |
| 2015/0316204 A1 | 11/2015 | Doyle | |
| 2016/0081871 A1 | 3/2016 | Doyle | |
| 2016/0339583 A1 | 11/2016 | Van Engelhoven et al. | |

FOREIGN PATENT DOCUMENTS

| | | | |
|---|---|---|---|
| EP | 0959826 B1 | 5/2003 | |
| EP | 2942044 A2 | 11/2015 | |
| EP | 3 156 193 A1 | 4/2017 | |
| EP | 3504033 B1 | 3/2023 | |
| GB | 2472036 A * | 1/2011 | ............... A61F 5/01 |
| JP | H04304979 A | 10/1992 | |
| JP | 07107861 A | 4/1995 | |
| JP | 2002153115 A | 5/2002 | |
| JP | 2008-295696 A | 12/2008 | |
| JP | 2009-106270 A * | 5/2009 | ............ A01G 17/00 |
| JP | 2009-268839 A | 11/2009 | |
| JP | 201118896 A | 9/2011 | |
| JP | 3184245 U | 6/2013 | |
| JP | 2014-503320 A | 2/2014 | |
| JP | 2017024086 A | 2/2017 | |
| WO | 2014093408 A2 | 6/2014 | |
| WO | 2014/195373 A1 | 12/2014 | |
| WO | 2015084177 A1 | 6/2015 | |
| WO | 2016065350 A1 | 4/2016 | |
| WO | 2017093298 A1 | 6/2017 | |
| WO | 2018/073629 A1 | 4/2018 | |
| WO | WO 2018/082906 A1 * | 5/2018 | ............... A61F 5/01 |

* cited by examiner

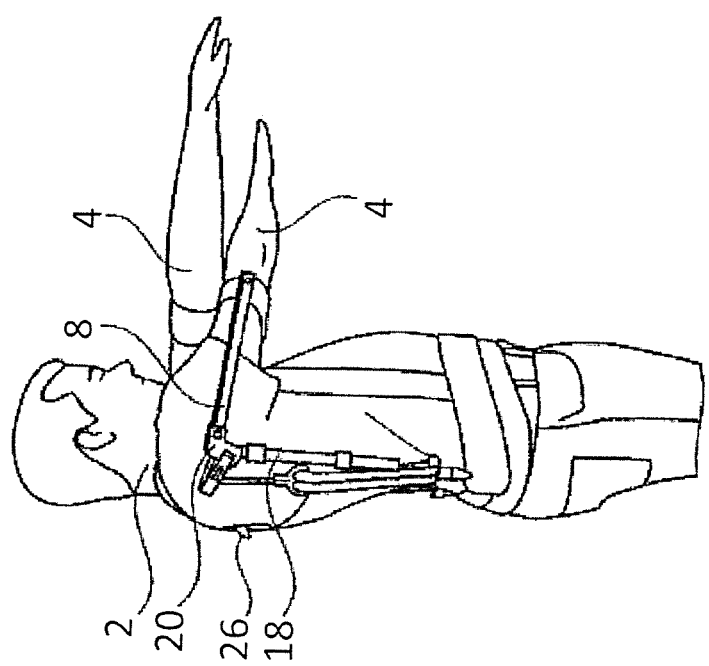

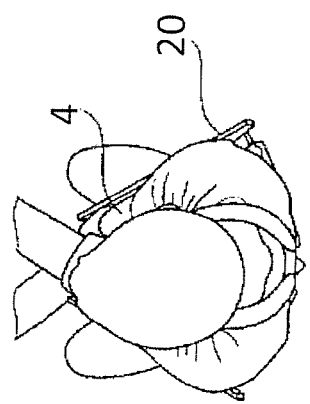
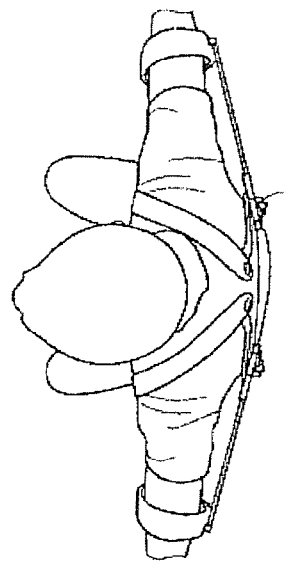
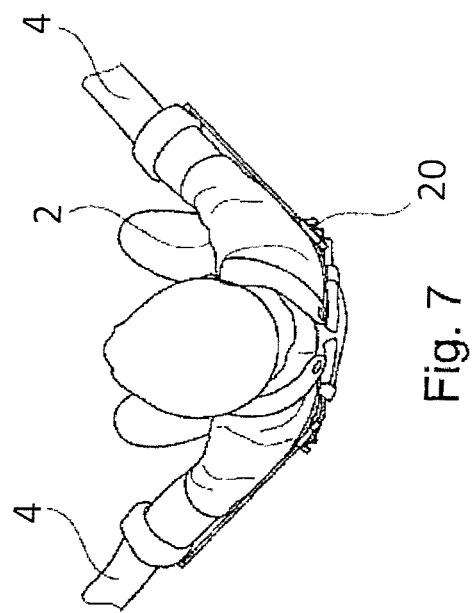

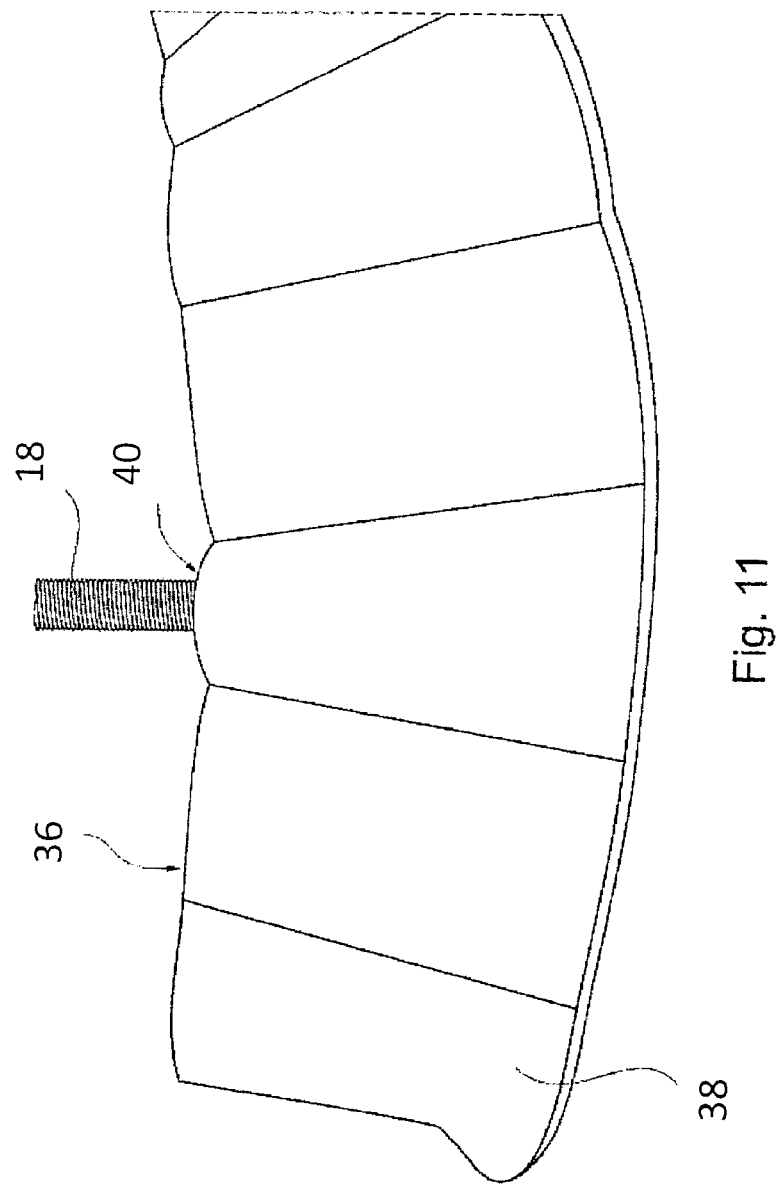

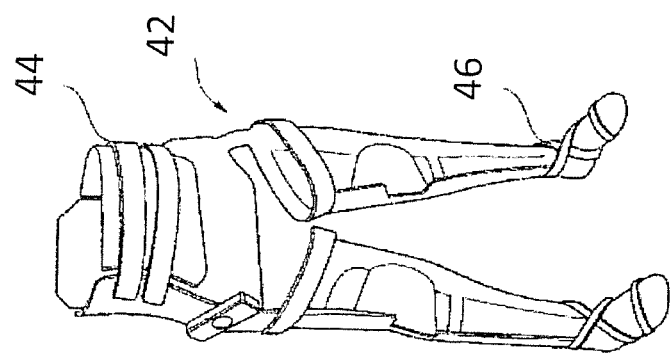
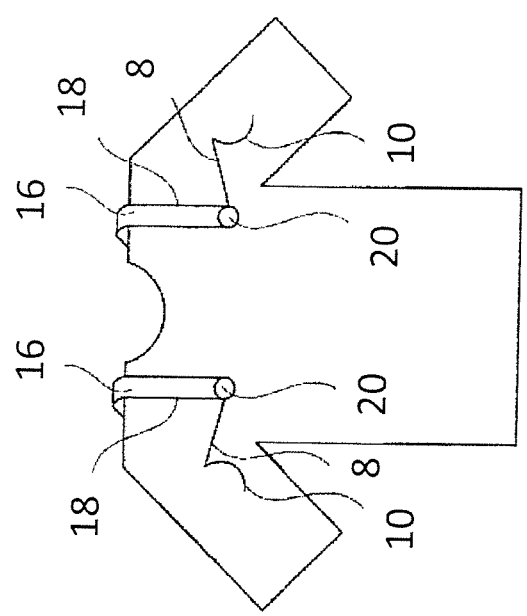
Fig. 13
Fig. 12

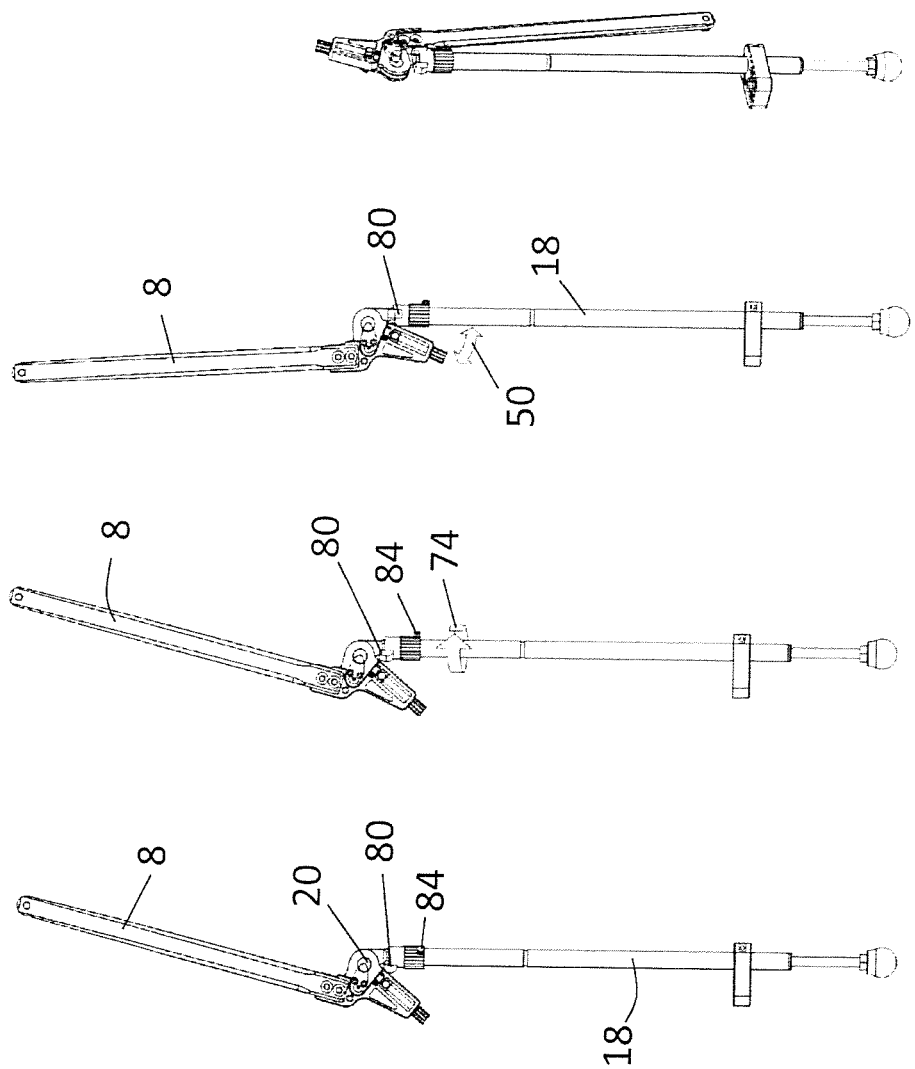

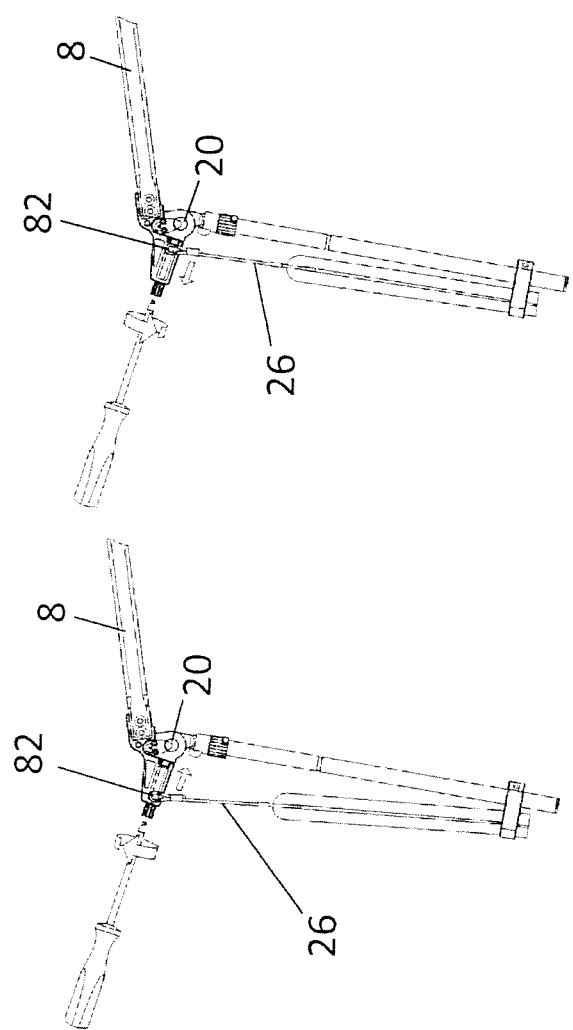

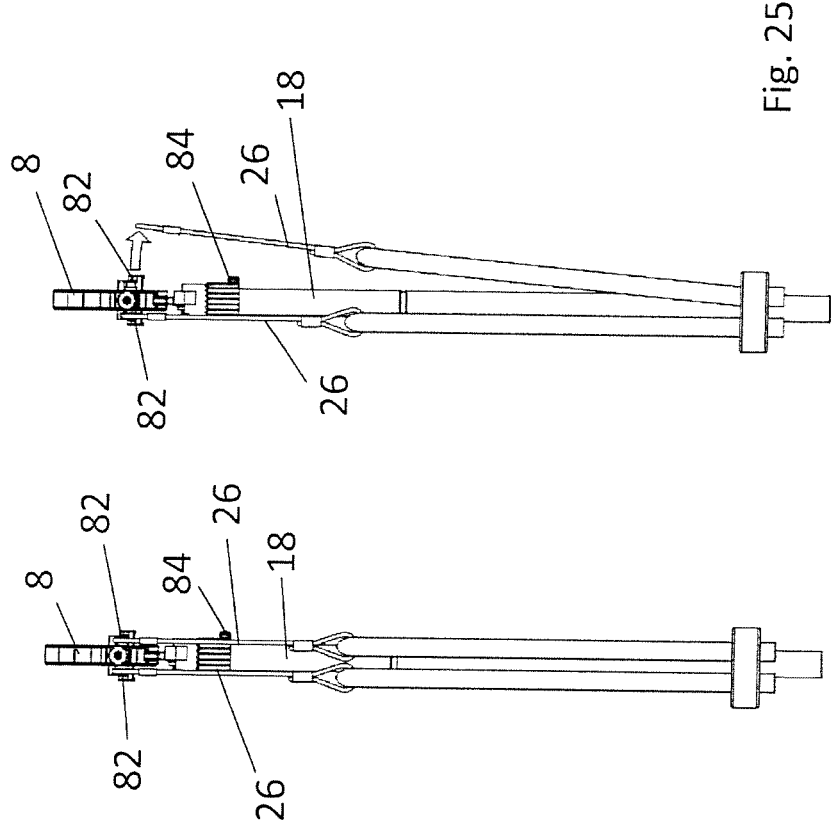

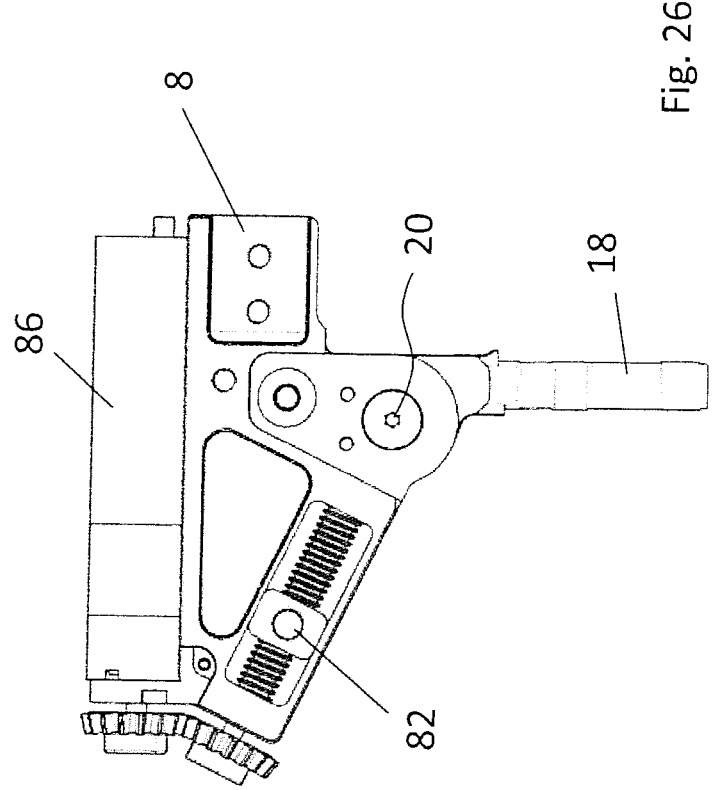

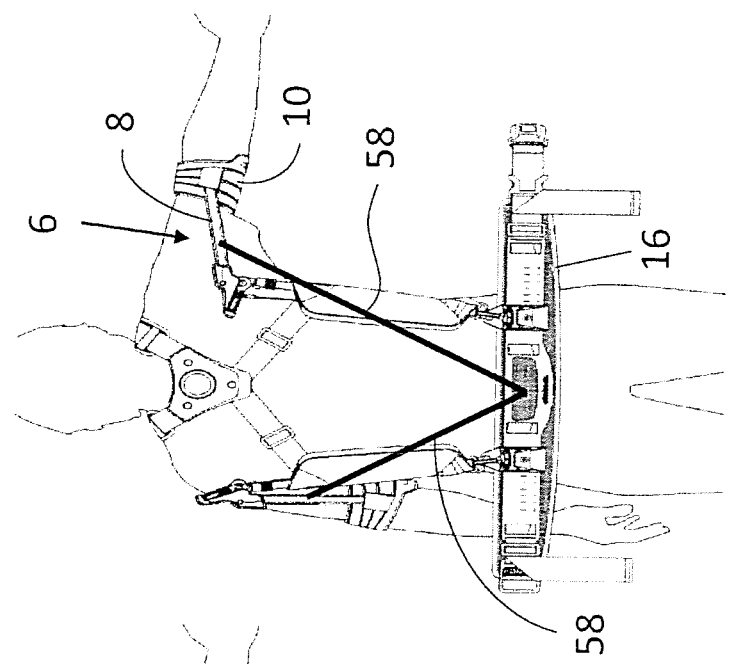
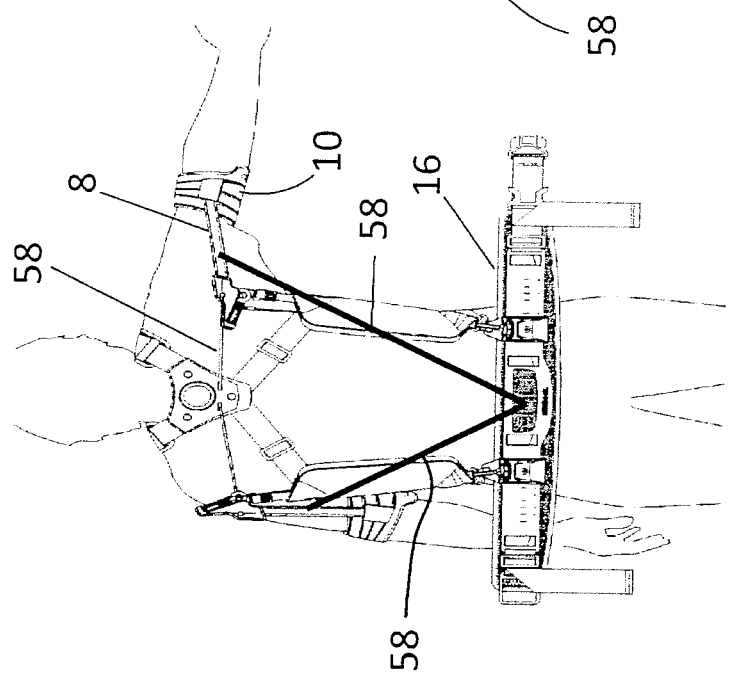

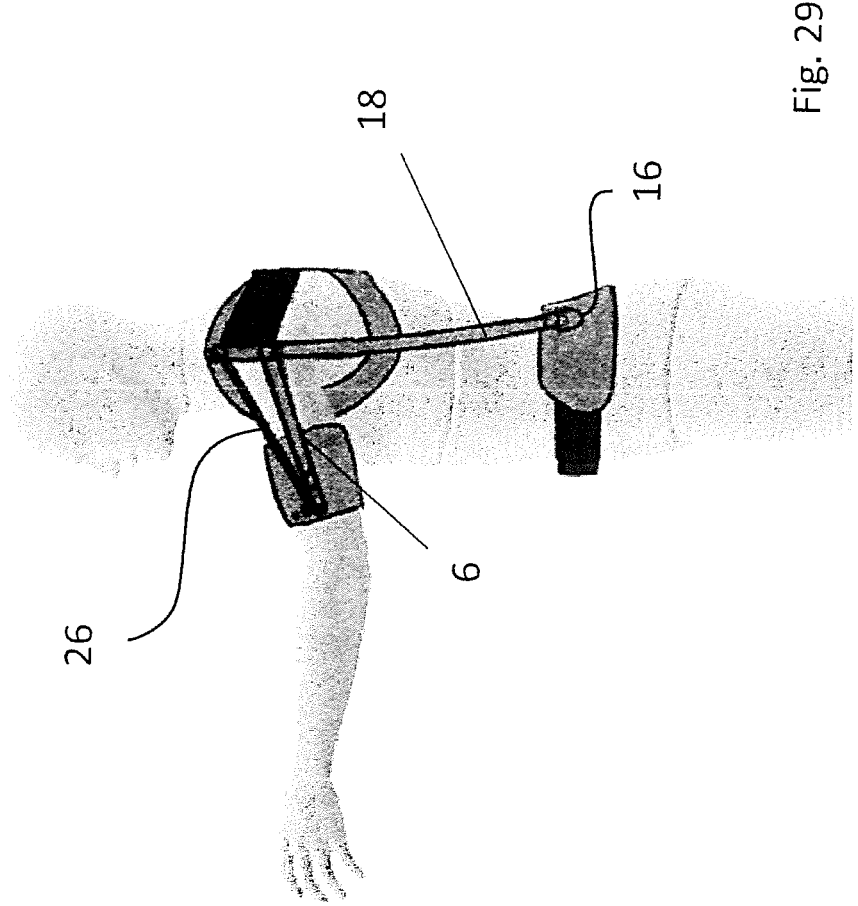

DEVICE FOR SUPPORTING AT LEAST ONE ARM OF A USER

FIELD OF THE INVENTION

The invention relates to a device for supporting at least one arm of a user, wherein the device has at least one arm support element with an arm shell for placing on the arm, at least one passive actuator that is configured to apply a force on the at least one arm support element and at least one counter bearing for the force to be applied, said counter bearing having at least one counter bearing element and at least one force transmission element that is configured to transmit a counter-force to the counter bearing element.

BACKGROUND

This type of device is described, for instance, in US 2016/0081871 A1. It features a counter bearing element that is designed in the form of a strap that can be placed around torso of the user. Two support braces run along the user's back to his shoulder, each of said support braces being connected to a joint above and laterally next to the shoulder of the user, such that the arm can be raised. Spring elements are arranged on the corresponding joints, by means of which an upward force can be exerted on the arm shells, such that the arms can be supported, for example when lifting heavy objects or when working above one's head. If the arms are lowered, a pressure must be exerted by the arms onto the arm shells, wherein this pressure exceeds the force applied by the spring elements, thereby causing the arms to lower.

WO 2014/093408 A2 and U.S. Pat. No. 9,427,865 B2 describe an equivalent device, each of which features a spring, especially a tension spring, that is connected to a Bowden cable, said spring functioning as a mechanical energy storage device which acts a passive actuator. The Bowden cable is guided by way of a pulley in such a way that, upon a swivelling of an arm, meaning a movement of the arm support element relative to the counter bearing element, the spring is stretched, such that the mechanical energy storage device is charged with energy.

In particular, if the user of the device trips or falls for instance and has to roll over, for example, these types of device may be hazardous for the user and lead to injuries. This may occur even though the joints of the device that are arranged outside of the shoulder joint are, according to the prior art, arranged as precisely as possible so that their joint axes and swivel axes pass through the corresponding axis of the shoulder joint, such that supposedly all movements that the natural shoulder and hence the arm of the user can execute can be imitated.

An active device that supports arms while work is being performed above a user's head is described in EP 3 156 193 A1. The arm shells are connected to one another by a number of different joints and connecting frame elements. This should render as many movements as possible which are executable by a shoulder joint also possible with the mounted device. However, due to the number of elements, the device is large, structurally intricate and therefore expensive. It must also be noted that the device tries to imitate the shoulder joint by way of two hinge joints. This means that not all movements that a natural shoulder joint can carry out are possible. In particular, when it comes to raising the arm in a specific direction, the joint that is to conduct the movement must first of all be moved into the right position so its swivel axis points in the desired direction. This may require the execution of additional and un-natural movements, which reduce the user's level of comfort and therefore also his acceptance of the device.

Further support devices, especially devices which support the lifting of heavy objects or work performed above a user's head, are known from WO 2014/195373 A1 and US 2016/339582 A1. However, these devices are only intended for specific movements for which support is deemed necessary.

SUMMARY

The invention thus aims to remedy these disadvantages or at least to reduce them.

The invention solves the task at hand by way of a device which is characterized by the fact that a freedom of movement of the spine of the user is not restricted by the device, wherein, in particular, an inclination is possible and/or the freedom of movement of the arm is not restricted by the device.

The invention also solves the task at hand by means of a device characterized by the fact that the at least one arm shell can be moved in relation to the at least one counter bearing element in at least three translational and three rotational degrees of freedom.

It is especially preferable if the arm support element is connected to the force transmission element via a joint, such that it can be swivelled about at least one swivel joint. The at least one force transmission element is preferably arranged on the counter bearing element such that it can be moved relative to the counter bearing element, in particular it can be rotated about at least one rotational axis To this end, the at least one force transmission element can be fixed to the counter bearing element by way of a hinge, a ball joint or another joint for instance, or for example plugged or inserted at one end of the force transmission element into a pocket or bracket on the counter bearing element specifically provided for that purpose.

The invention is based on the knowledge that, in spite of the often complex and intricate arrangement of joints, such orthoses and devices are not capable of imitating many movements in the shoulder region of the wearer. This applies especially to movements during which the orientation and/or position of the at least one arm support element relative to the counter bearing element changes, and which are not or not only caused by a movement of the shoulder, but for example by movements of the torso, the spine or the shoulder girdle. In the situations described, in which the user trips or falls, these movements are of particular importance with regards to breaking the fall and avoiding injury.

In particular, it is based on the knowledge that, for the device described in EP 3 156 193 A1, the hinge joints require a fixed reference point to the anatomical joints and the pivot points are thus firmly fixed by the frame.

The movability of the at least one force transmission element relative to the counter bearing element means that, in a preferred configuration of the device, the freedom of movement of at least one arm is not restricted by the device.

Within the scope of the present invention, the notion that the freedom of movement of the arm is not restricted by the device should be understood especially to mean that every movement which the user of the device can execute without a device is also possible with the device; the user is therefore restricted to, at most, a minimal degree, i.e. not significantly. In particular, these movements include anteversion and retroversion, i.e. the raising of the arm forwards and backwards, abduction and adduction, i.e. the raising and lowering of the arm in a lateral direction, and the internal and external rotation in the shoulder joint. In particular, a device according to the invention renders possible a circumduction to the same degree as can be performed by the person without the device. A circumduction is the circular movement of the arm about the primary executable movements of the three joint axes, in particular at maximal movement deflection, which results in an irregular cone, the tip of which lies in the shoulder joint.

The notion that the freedom of movement of the user's spine is not restricted by the device should be understood particularly to mean that an inclination and a reclination are possible. These movements are also referred to as ventral flexion and dorsal extension. An inclination is the leaning forward of the upper body, and thus of the spine and the head, while reclination is the opposite movement. Other movements of the upper body and therefore the spine, such as lateral flexion and rotation, are preferably not restricted by the device either.

Movements of the spine, particularly a leaning of the spine to the side and/or forwards and backwards and/or a twisting of the spine about its longitudinal axis, are preferably not prevented, restricted or rendered impossible by the device either. All of the movements described here are preferably restricted by the device in neither their maximum movement deflection nor in a sequence of movement.

In this case, the arm shell can be moved in at least three translational and three rotational degrees of freedom in relation to the at least one counter bearing element. While devices known from the prior art allow at most rotational degrees of freedom, the device according to the invention also enables movements of the arm shell relative to the counter bearing element, such movements comprising solely a translational movement along a direction in space, for example. As a result, the arm shell can trace and perform movements of the upper arm relative to the counter bearing element, wherein these movements are not only the result of movements of the shoulder, but also require a movement of, for example, the spine or another body part.

In a preferred configuration of the device according to the invention described here, the force transmission element features a compression force transmission element, especially a rod or a splint, on which the arm support element is arranged such that it can be swivelled about a swivel axis. In this case, it is often sufficient to provide a single hinge joint with a swivel axis. Complicated structures comprising several joints, whose swivel axes meet at a point, preferably virtually at the pivot point of the ball joint of the natural shoulder, are not necessary. This considerably simplifies the structure and allows for a reduction in production costs.

The joint via which the arm support element is arranged on the force transmission element, and the counter bearing element are preferably positioned at a distance from one another via the force transmission element. The distance corresponds to the effective length of the force transmission element. In this case, when the device is in the mounted state, the joint is situated approximately at the height of the user's shoulder joint. When the device is mounted, the counter bearing element, especially the joint device of the counter bearing element, by means of which the force transmission element is arranged on the counter bearing element, is preferably situated in a pelvic region of the user; it is especially preferable if it is situated on or below the iliac crest and above the hip joint of the user. Here, the shoulder region specifically includes the user's shoulder blade. The joint is preferably situated at the same height as or higher than the glenoid cavity.

It is preferably possible for the joint to execute a movement range that passes the user's shoulder, thereby ensuring that the joint does not strike the body, even if the arms are in extreme positions. In particular, this is achieved by way of the comparatively large distance between the arm shell of the arm support element and the counter bearing element. The arrangement of the counter bearing element in the user's hip region allows for forces acting on the counter bearing to be easily absorbed and diverted via the pelvis. This prevents soft parts or ribs from pressing into the user's upper body. To this end, the counter bearing may comprise a pelvic strap which is connected, in particular flexibly, to the force transmission element.

The arm support element preferably has a sleeve which, when the device is mounted, can be connected to the user's arm. This sleeve has a longitudinal extension or length along the direction of the arm that is to be inserted into it. The middle of this longitudinal extension or length is hereinafter referred to as the middle of the sleeve.

In the same way, an arm shell also has a longitudinal extension or length, the middle of which defines the middle of the arm shell. The distance s describes the distance between the middle of the sleeve or the middle of the arm shell on the one hand and a rotational axis of the joint, via which the arm support element is fixed to the force transmission element, on the other. The distance a describes the distance between the rotational axis of this joint and the position at which the force transmission element is fixed to the counter bearing element. The ratio a/s of the two distances is preferably greater than or equal to 1.1, preferably greater than or equal to 1.3, more preferably greater than or equal to 1.4 and especially preferably greater than or equal to 1.5. The ratio a/s of the two distances is also preferably smaller than or equal to 5.0, preferably smaller than or equal to 3.0, more preferably smaller than or equal to 2.5 and especially preferably smaller than or equal to 2.0. For this purpose, when several sleeves or arm splints are provided, the sleeve or arm splint that is arranged furthest away distally is considered.

Due to these dimensions, the introduction of a force into the arm occurs by way of a sufficiently large lever arm between the sleeve or the splint on the one hand and the joint on the other, while the force resistance on the counter bearing that is needed for this to happen occurs far enough away from the shoulder region of the user, in particular in the hip region of the user.

It is especially preferable if the counter bearing element, which in particular is designed as a pelvic strap, features padding that faces towards the user's body, wherein the padding is preferably adjusted to the anatomical form of a pelvic bone. The padding has, for instance, a recess for at least partially accommodating an iliac crest of the ilium (os ilium) of the pelvis. This prevents or at least reduces a pressure, which may be painful, on protruding parts of the pelvis. Due to the fact that, as a result of the adjusted contouring of the padding, the padding has a natural, particularly comfortable position relative to the pelvis, the device can be correctly placed by the user in an intuitive manner, rendering it easier to operate.

Preferably, the counter bearing element is at least partially made up of a belt that can be guided through the belt loops on a pair of trousers. The counter bearing element can therefore be fixed to the user's trousers. This ensures that the counter bearing element can be securely positioned in the user's hip region. To this end, the counter bearing element may for example protrude from a connection point between the force transmission element and the counter bearing element, which is particularly designed to be a ball joint that is connected to the counter bearing element, by a length and width which allow for the counter bearing element to be fed into at least one of the front belt loops on a pair of trousers. At its free end, the counter bearing element may have a width of 3.0 cm±1.0 cm for example, in particular 3.5 cm±0.2 cm. In an especially preferable configuration, the end of the force transmission element that is connected to the counter bearing element is inserted only into a pocket on the counter bearing element. In this case, the force transmission element can be removed from the pocket when it comes to mounting the device, such that the counter bearing element can be easily guided through the belt loops on a pair of trousers until the final position has been reached. The force transmission element can then be simply inserted into the pocket of the counter bearing element.

The joint is preferably configured to move away from the user's body to allow for an abduction and/or adduction of the arm. In this case, the user moves the arm away from the body in a frontal plane. This causes a distance of the joint from the body of the user to increase, in particular by way of a movement of the joint away from the body in the horizontal direction, especially within a transverse plane. Here, the force transmission element is swivelled relative to the counter bearing element about the connection point at which the force transmission element is fixed to the counter bearing element. This swivelling occurs because the swivel axis of the joint between the arm support element and the force transmission element does not correspond to the joint axis of the user's shoulder, about which the abduction and/or adduction occurs. A rotation of the arm support element about the longitudinal axis of the force transmission element preferably occurs at the same time.

It is especially preferable if the distance of the joint from the body of the user is essentially at its maximum when the arm is extended in the horizontal direction away from the body. If the arm is raised further, the joint preferably moves back towards the body. The minimum distance between the joint and the body of the user is preferably reached in the two end positions of the abduction and/or adduction. These end positions are defined by a striking of the arm on the user's head and a striking of the arm on the user's hips. In these end positions, the joint is far enough away from the user's body so as not to press against it.

A maximum distance of the joint from the body is preferably conceived for the situation in which the arm is extended in the transverse plane. The movement away from the body prevents the joint from striking the body of the user, thereby making the device more comfortable to wear. Since the positions of the arm are known at which the maximum and minimum distance of the joint from the body of the user are reached, the selection of the length of the spacer element on the one hand and of the force transmission element on the other can be used to set the maximum and/or minimum distance. If the maximum distance is set to be as small as possible, the risk of an inadvertent striking of the joint against another object while the user is performing an activity is minimized. In the event of an abduction and/or adduction of the arm, the joint can be shifted, in particular completely or predominantly, within the transverse plane. However, it is also possible that the joint is shifted at least partially in the sagittal plane and/or the frontal plane, for example to enable as simple and robust kinematics as possible between the arm shell and the counter bearing element.

When the device is in the mounted state, the joint, by means of which the arm support element is connected to the force transmission element, is preferably located in a shoulder blade region, preferably on the shoulder blade, of the user. However, this does not mean that the joint, when mounted, is in contact with the body of the user; rather, this contact would only occur on the user's shoulder blade if the joint were to be pressed onto the user's body.

The joint is preferably configured and arranged in such a way that it swivels within its transverse plane when the arm is moved in a transverse plane. If the user's arm protrudes laterally from the body in the transverse plane and is swivelled within the transverse plane in front of the body, the joint traces this swivel movement in the transverse plane. To this end, the joint is preferably moved away from the shoulder region of the user and guided about the shoulder joint. This is also preferably achieved by way of the flexible fixing of the force transmission element on the counter bearing element. Here, the force transmission element is swivelled relative to the counter bearing element about the connection point at which the force transmission element is fixed to the counter bearing element. A rotation of the arm support element about the longitudinal axis of the force transmission element preferably occurs at the same time.

In this preferred configuration, the joint is essentially guided along a comparatively short distance on the shoulder joint. A striking of the joint on the body of the user is hereby prevented, thus making the device more comfortable to wear. In addition, there is a low risk of an inadvertent striking of the joint against another object while the user is performing an activity.

If the arms cross to a maximum extent in front of the user's body, the joint is situated essentially laterally next to the body, in particular at shoulder blade height. If the user's arm protrudes laterally from the body in the transverse plane, the joint is positioned at the back of the body, in particular at shoulder blade height. During the swivel movement of the arm in the transverse plane, the joint is swivelled, in particular completely or largely, in the transverse plane along a trajectory. A movement in the transverse plane then occurs when the force transmission element is perpendicular to the transverse plane.

During operation of the device, the counter bearing device is placed on an object to which the acting force should be transmitted. Given that the passive actuator is to apply a force on the arm support element, a corresponding counter bearing must be provided on which it can be supported. A passive actuator within the meaning of the present invention is specifically not a motor. The required energy it needs to apply the force is produced by the user or wearer of the device. Generally speaking, the force that is to be applied to the arm support element counteracts the force of gravity. When the arm and the connected arm support element are raised, energy is withdrawn from an energy storage device of the passive actuator. When the opposite movement is executed, i.e. a lowering of the arm, this occurs against the applied force. The energy storage device of the passive actuator is supplied with energy. For a passive actuator within the meaning of the present invention, this is the only source of energy when an adjustable preload of the energy storage device of the passive actuator does not occur.

The passive actuator preferably features at least one energy storage system, preferably at least one mechanical energy storage system. For instance, this may comprise a spring element, a pressure accumulator, a pneumatic and/or hydraulic system and/or a hydraulic energy storage system. The spring element, for example, may be arranged directly on the joint between the compressive force transfer element and the arm support element in the form of a rotational spring or a constant force spring. Elastic elements in the form of elastic cables, such as rubber cables, are also conceivable, one end of which is arranged on a part of the arm support element. If the arm support element is swivelled about the swivel axis relative to the compressive force transfer element, the elastic element is stretched or compressed, such that energy is either supplied to or withdrawn from the mechanical energy storage system. Of course, other elements, such as gas springs or compression springs, are also conceivable, for which a deflection is used to transform the compressive force coming from the compression spring into a tensile force.

The mechanical energy storage system may be arranged at various positions on the device. Preferably, a position is selected at which the installation space required for the energy storage device is available and the energy storage device does not cause any disruption, even while the user's arm is moving. Accordingly, it may be arranged on the upper arm, for instance.

In a preferred configuration, the counter bearing element is a mounting element, especially a strap, a belt, a bandage or a shell element, for placing the device on a body part, in particular a torso of the user. The mounting element is preferably integrated into an item of clothing, such as a pair of trousers. Alternatively or additionally, the counter bearing element comprises at least one shoulder element for placing the device on a shoulder of the user. Alternatively or additionally, the counter bearing element has at least one ground contact element, thereby enabling the counter force to be introduced into the ground. Such ground contact elements are preferably designed as exoskeletons and are known from the prior art. It may be designed to be active, for instance motor-driven, or passive.

If the counter bearing element is designed as a mounting element for the user's torso, especially the user's hips, the required counterforce can be diverted in a way that is particularly comfortable and convenient for the user. It is introduced into the body of the user via the hip region and absorbed by the legs. The deployment of a ground contact element is especially advantageous if the device is used to support during the lifting of heavy loads. In this case, were the counter bearing element designed as a mounting element for the torso, especially the hips, of the user, the additional strain caused by the heavy load would indeed be diverted by the shoulder region of the user; however, this would have to continue through the legs. This can be remedied via the use of at least one ground contact element. In this case, it is possible to divert at least part of the strain, yet preferably the complete additional strain, into the ground, the result being that the user's legs and in particular his knees are not overburdened. To this end, orthoses such as active or passive exoskeletons, the principle of which is known from the prior art, can be used, wherein these orthoses extend from the hips, via the knee and the ankle, down to the user's foot.

The use of a shoulder element for placing on the shoulder, which may be configured in the form of backpack straps or suspenders for example, allows for an especially small construction of the device. However, it does have the disadvantage that the forces that are actually to be diverted from the shoulder region are actually introduced into the shoulder region at another point, thereby reducing the effect cornpared with the use of another counter bearing element. Of course, the counter bearing element may also be a flexible or rigid element that is to be arranged on the shoulder or another part of the human body, in particular another part of the user's torso.

It has been proven to be advantageous if the orientation of the force transmission element can be changed relative to the counter bearing element by way of a movemnt of the torso and/or a movement of the arm of the user. As a result of this change in orientation, such as a change in a direction of longitudinal extension or an angular position of the force transmission element relative to the counter bearing element, it is possible to realize a number of movements and degrees of freedom, preferably all movements and degrees of freedom, which cannot be achieved by the swivelling arrangement of the arm support element on the compressive force transmission element. The fact that the change in orientation is achieved simply by a movement of the torso and/or arm of the user ensures an intuitive operation of the device. The compressive force transmission element is preferably connected to the mounting element by means of a joint, especially a ball joint or a hinge. The exact configuration of this joint depends on its intended purpose and the circumstances, in particular the individual preferences of the user. A ball joint may be used which enables a swivelling of the compressive force transmission device, which is designed as a rod or a pole for example, relative to the mounting element, which is designed as a belt or a strap for example. This type of joint may also allow for a torsion, i.e. a rotation of the compressive force transmission element about its own longitudinal axis. However, where applicable, the provision of a simple hinge joint shall suffice, the compressive force transmission device being arranged on the attachment element via said hinge joint. In particular, this shall suffice if the mounting element is so flexible that it still enables a movement of the compressive force transmission element relative to the mounting element, this movement resulting in a deformation of the mounting element. Given that the mounting element itself is designed to be a flexible element, this deformation is reversed upon a corresponding movement of the user's arm and/or torso. As a result, at this point, as simple a connection as possible between the compressive force transmission device and the mounting element is achieved.

The joint, via which the compressive force transmission device is arranged on the arm support element, may be designed in a different way. It may be designed as a prismatic joint or chain joint, or as a folding mechanism. Elastic elements, such as bending springs, may also be used as joints and at least also as mechanical energy storage devices at the same time. Of course, the Bowden cable principle, for instance in the form of a push-pull cable, can also be used.

The arm support element comprises the arm shells that are preferably arranged on a spacer element. This spacer element, as part of the arm support element, is preferably connected to the compressive force transmission element or the force transmission element. The lengths of the compressive force transmission element, which is designed as a splint or rod for example, and where applicable of the spacer element which is designed as a rod or splint, are preferably selected such that the entire angular range of the potential movement of the upper arm of the wearer is covered. The arm shell is preferably flexibly arranged on the spacer element to render the device as comfortable as possible to wear.

In a preferred configuration, the passive actuator is configured to apply the force depending on a position and/or orientation of the at least one arm support element relative to the counter bearing element, especially depending on a swivel angle of the arm support element about the swivel axis, wherein the passive actuator preferably applies the force to the arm support element eccentrically. The force is preferably applied to the spacer element of the arm support element. Instead of using, for example, a constant force spring as a passive actuator, by means of which the same force is always applied regardless of the position and angular position of the upper arm and thus also of the arm support element, passive actuators may be used by means of which different forces may be applied depending on the position and/or orientation of the arm and thus the arm support element. In this way, it is advantageous, for instance, to not apply a force so long as the arm does not exceed a certain angle relative to the normal, i.e. the direction that follows the laws of gravity. This angle may be 45°, 60° or 90°, for example. Only when the arm is raised beyond this angle is a force preferably applied by the passive actuator, said force counteracting the force of gravity. This force may vary with the continued raising, i.e. swivelling, of the upper arm and thus the arm support element relative to the compressive force transfer element. To this end, cam discs, gears or other force-path-functions, such as slots, may be used. A maximum force is preferably applied within an angular range of 70° to 120°, especially preferably at 90°.

Preferably, the force that can be applied by the passive actuator can be altered by way of an alterable preload of the passive actuator and/or an adjustable eccentricity of the application of force on the arm support element.

In a preferred configuration, the force transmission element is mounted in a guide which prevents the part of the force transmission element on which the arm support element is arranged from moving away from the user's torso when the device is mounted. In a structurally particularly simple configuration, the guide refers to a loop or a sleeve that is preferably made of a fabric. The guide preferably serves as a positioning aid. A movement of the force transmission element relative to the guide is beneficial but not necessary.

It is especially preferable if the device features two arm support elements for supporting both arms, wherein each of the two arm support elements has an arm shell and is preferably arranged on a force transmission element such that it can be swivelled, and wherein at least one connection element is preferably arranged between the force transmission elements, by means of which a tensile force can be preferably applied to both force transmission elements. This also prevents the end of the force transmission elements facing away from the counter bearing from moving too far away from the body, especially the torso, of the user.

If the device relates to a device for supporting two arms of a user, the device has two arm support elements, each of which has an arm shell for placing on the arm, at least one passive actuator that is configured to apply a force on at least one of the arm support elements and at least one counter bearing for the force to be applied, which features at least one counter bearing element and at least two force transmission elements that are configured to transmit a counter-force from one of the arm support elements to the counter bearing element. In this case, the device preferably comprises two passive actuators, each of which is configured to apply a force to one of the arm support elements.

It is particularly preferable if the two force transmission elements can be moved independently of one another relative to the counter bearing element. This renders it possible to follow various movements that the user of the device makes with both arms.

There is preferably no rigid coupling between the force transmission elements. The two joints that connect the two arm support elements with the two force transmission elements can therefore move away from or towards each other if the arm movements stipulate as such.

A swivel range of the joint can preferably be restricted by an end stop. The end stop preferably restricts a movement of the arm support element relative to the force transmission element about the swivel axis. The device preferably comprises two end stops, each of which restricts the movement of an arm support element about the swivel axis relative to the respective force transmission element. This prevents an overshooting of the various structural components relative to one another, for example if the verticals are surpassed.

The end stop can preferably be moved into an active position, in which it restricts the movement, and a passive position, in which it does not restrict the position. In particular, the end stop can be fixed—preferably locked—in the active and/or passive position. This renders a varying degree of freedoms of movement possible for storing the device, mounting and removing the device and/or using the device. A high degree of freedom of movement may render it easier to store and/or transport the device with as small a packaging volume as possible. A low degree of freedom of movement may prevent the occurrence of unfavorable relative positions, for example when mounting and removing the device, these positions being the result of a preload of the passive actuator, for instance.

It is especially preferable if the end stop is a projection on the force transmission element. A part of the joint that is connected via the arm support element, such as a protruding attachment, may automatically strike the force transmission element if the predetermined maximal swivel range is surpassed. In a configuration of the present invention, the force transmission element is rotated about its longitudinal axis in order to bring the projection into the active or passive position. A conscious rotation of an end of the force transmission element that is attached to the joint can activate or deactivate the functionality of the end stop.

In particular, the force transmission element comprises an upper section that is connected to the joint and a lower section that is coupled with the counter bearing element, wherein the end stop is designed to be on the upper section and the upper section is configured such that it can be locked at different angular positions relative to the joint. In this case, the upper section is coupled with the joint in such a way that it cannot be twisted about its longitudinal axis. However, this rigid coupling can be refrained from in order to fix the upper section in an angular position relative to the joint, wherein the section has been twisted about its longitudinal axis. This twisted fixing of the upper section to the joint preferably results in a relative movement of the end stop to the joint. In this configuration, this causes a movement of the end stop between the active position and the passive position. The lower section is preferably coupled with the counter bearing element such that it can be rotated, wherein the upper section and the lower section are connected to one another such that they are torque-proof during normal operation so as to enable a swivelling of the joint about a connection point between the force transmission element and the counter bearing element. To bring the end stop into the active and/or the passive position, the upper section can be twisted relative to the joint and the lower section. To this end, an anticipated friction between the upper section and the lower section must be overcome, for instance, wherein this friction can keep the end stop in the active and/or passive position via frictional locking. Additionally or alternatively, an operable locking device, such as a detachable catch device, is preferably provided which, when open, allows for a rotation of the upper section and, when closed, blocks a rotation of the upper section by way of frictional and/or positive-locking.

The upper section is preferably coupled with the lower section via a spiral-shaped coupling for the purpose of shifting the end stop in the longitudinal direction of the force transmission element between the active position and the passive position. For example, the upper section is coupled with the lower section by way of a screw thread, such that a relative rotation of the upper section to the lower section of the force transmission element can be telescoped to the extent that the end stop can be shifted between its active position and its passive position by at least one movement in the longitudinal direction of the force transmission element.

In particular, if two arm support elements and two force transmission elements are provided, these may also be arranged in two-dimensional layers, for instance in the shape of a cross. It is also possible to use several supports or springs, elastic or mechanical energy storage devices or other force transmission or force application elements. The two-dimensional arrangement means that, when in the mounted state, the device is not particularly bulky and is thereby less disruptive during day-to-day activity. Moreover, it enables the force transmission elements to more easily follow the movements of the user's torso.

The device can preferably be adjusted to fit different physical dimensions of the user. As a result, the device is versatile and flexible; there is also no need to provide different devices for users with varying physical dimensions. For example, the length of the force transmission element, especially in the form of the compressive force transmission element, can be adjusted by way of telescopic rods, for instance. These may comprise quick-release levers or swivel locks, rendering an unlocking, adjustment of length and subsequent locking very easy. This is preferably provided in an infinitely variable configuration. However, it is also possible to provide separate grades of adjustment. For instance, locking bores may be provided with which a pin—which is spring-loaded from within—engages when the desired length has been set. In order to adjust the length, the pin is pushed into the telescopic rod and the numerous elements of the telescopic rod are shifted relative to one another.

Of course, the length of the spacer element of the arm support element can also be adjusted in the same way. A telescope or a telescopic rod can also be used for this purpose. Alternatively or additionally, the arm shell may be designed to slide on or in the spacer element in order to compensate for incongruencies. In this case, certain movements of the upper arm relative to the shoulder result in a movement of the arm shell relative to the distance element, such that the arm shell always comes into contact with the arm of the user in the same region.

Alternatively to a telescopic rod, inter-twisted spirals or pivot bearings on the upper arm can be used to set the length and direction.

The joint, by means of which the force transmission element is arranged on the mounting element, is preferably securely mounted on each mounting element. If said element is designed to be a strap or a belt, its length is easily adjusted, meaning that the position of the joint is also easily adjusted. Alternatively or additionally, the joint—which may be designed as a clip for example—can also be connected or is connected to the mounting element such that it is detachable. Alternatively or additionally, it may be configured in such a way that it can be shifted along a splint, a slot or another contour. Other possibilities include the arrangement inside a belt pouch, the coupling of the joint via a so-called ratchet closure, as is common with ski boots for example, as a pin fastener or via a velcro fastener.

It is especially easy to identify the right size of the device if the device is integrated into an item of clothing, especially a jacket or a shirt. In particular, the mounting element is preferably integrated into a pair of trousers. In this case, only the user's clothing size need be identified for items of clothing in the right size to be selected.

Given that forces of various strength must be applied by the actuator for users of varying size and strength, it has been proven advantageous if the strength of the force to be applied is adjustable. This may be achieved, for example, by ensuring that a preload of a spring element, such as a coil spring, can be adjusted via a rotating dial or a sliding mechanism, for instance. The length of a slackened spring, i.e. the length of the spring without a load, is also adjustable. Alternatively or additionally, several coils or spring elements may be provided that can be activated either individually or collectively, and which may—but do not necessarily have to—feature different spring constants and degrees of hardness. The length of a lever arm, which is subjected to the force applied by the passive actuator on the arm support element, especially on the spacer element of the arm support element, can also be adjusted and, for example, altered by way of a setscrew. The same applies for the end stop of a Bowden cable. The setting may be executed mechanically or mechatronically, for instance by way of a motor. The mechatronic adjustability is advantageous, for example, if the applicable force is to be adaptively adjustable, such as if a greater supporting force is required or desired because an item, such as a tool, is being held.

It has been proven especially convenient if the spring elements and the other mechanic, hydraulic or pneumatic energy storage devices are not tensioned until the device is mounted. They can also be slackened upon removal of the device. This may occur, for instance, by way of levers, loops or detachable clamping connections which are connected to the respective spring elements and, where applicable, allow for a tensioning of the spring to the desired degree. Alternatively or additionally, slides may be provided on which one end of the spring element is arranged, for example. By moving the slider along a guide element, the spring or the spring element can be tensioned or slackened. The locking and fixing in a particular position is preferably achieved by tilting the slide on the guide element.

It is especially preferable if the arm shell is a self-closing shell, which is open so long there is no arm inside it. If the arm is introduced into the shell, an activation mechanism is triggered which causes the shell to close. This mechanism can also be used to tension the spring elements.

The device preferably has a blocking device, by means of which a movement of the arm support element relative to the force transmission element can be blocked in at least one direction; preferably, the movement can be blocked completely.

At least one tension element, in particular at least one tension spring, is preferably situated between the arm support elements. As a result, a tensile force is exerted on each of the arm support elements that acts in the direction of the respective other arm support element. Surprisingly, this ensures that the force transmission elements do not move away from the torso of the wearer, even if the wearer of the device carries out complicated or unusual movements. This reduces the risk of components of the device hitting other objects or door frames for example, which would reduce the wearer's acceptance of the device. This may also prevent or at least reduce the risk of the arm support elements shifting too dramatically due to the not completely unavoidable incongruencies between the parts of the device and the body parts of the user of the device.

Preferably, at least one of the arm shells, but preferably both arm shells, features a fastening element, especially one that is designed as a strap. This fastening element is used to secure the arm shell around the arm. For instance, the strap can be wrapped around the arm and fixed at an opposite end of the arm shell by way of a fixing element that can be arranged at a free end of the strap and designed as a velcro fastener, for example. Of course, there are other ways to fix it, such as a clasp, a positive form locking element, for example in the form of a button, or other fastening elements.

The fastening element can preferably be fixed to another element, other than the arm shell of the device, by means of at least one fixing element. This other element is preferably a shoulder strap or a force transmission element or a cladding for one of these force transmission elements or the counter bearing element. If in this case the wearer of the device removes the device, he must first of all release the fastening element so he can remove his arm from the arm shell. Due to its structure, there is currently a risk that the removal of the arm from the arm shell would reduce the force applied via the arm to the arm support element, while the force applied by the passive actuator remains. This may result in a rapid, for example jerky, upward movement of the arm support element, which may result in injury or damage to equipment or objects in the surrounding area. However, if the arm shell is locked by way of the fastening element, the fastening element must first of all be released in order to remove the arm from the arm shell. The wearer of the device thus holds one end of the fastening element in his hand, the result being that a downward acting force continues to act on the arm shell and therefore also the arm support element. In this case, the fastening element is preferably arranged on a different element of the device, such as a shoulder strap. This enables the control of the device and, where appropriate, allows it to be brought slowly into a type of "parked position" without the occurrence of any jerky movements.

The reverse is carried out when mounting the device. The wearer of the device who wishes to mount the device must first of all release the fastening element from the other element of the device, thereby already applying a force on the arm support element in order to bring it in the desired position ready for mounting. In doing so, it is preferable if he does not let go of the fastening element until the arm is in the arm shell. The fastening element is then closed around the arm and the device is securely mounted.

The counter bearing element preferably features a strap which can be fastened by way of a fastener and that can be wrapped around a torso of the wearer. Such a strap constitutes a stand-alone invention and can be used on its own or as part of such a device, in particular as part of an orthosis or a prosthesis. In this way, such a strap can also be wrapped around a different body part of a wearer of the device or around an object. Such a strap is always advantageous, for instance, if the strap, when closed, is subject to such tension that an inadvertent opening of the strap would lead to a jerky and uncontrollable release of this tension. This refers to a hip or abdominal strap, for example. Here, the fastener is designed in such a way that it requires at least two steps to open and close it. For example, if a simple snap fastener were to be used as a fastener which can be released, for instance, by activating one or two activation elements, there is a risk that, as a result of the forces acting by way of the actuators, the ends of the strap would rapidly move apart, thereby hitting any objects or persons in the surrounding area. The fastener is designed to feature two steps in its operation to avoid such a situation.

One end of the strap is preferably guided through a loop arranged at the other end before a positive-locking fit of two correspondingly designed positive-locking elements is created to seal the fastener. In this case, it is preferable if one of the two positive-locking elements is arranged at the end that is guided through the loop. To open the fastener, the positive-locking fit must first of all be released, followed by the guiding of one of the ends of the strap through said loop, wherein the one positive-locking element is once again guided through the loop.

Preferably, the passive actuator features at least one elastic element and the device at least one mounting element which, at a predetermined angle between the arm support element and the force transmission element, fits closely on the elastic element, thereby changing the force that is to be applied to the arm support element. During a movement of the arm support element relative to the force transmission element, the elastic element exerts a force, as it is stretched or compressed. The support element is preferably mounted relative to the force transmission element such that it can be rotated and a point of application of the force applied by the elastic element lies eccentrically relative to the rotational axis of the corresponding joint. A swivelling of the arm support element relative to the force transmission element thus causes a change in the direction of the force applied by the elastic element. In particular, the mounting element, which is preferably arranged on the joint, is arranged such that it comes into contact with the elastic element at a predetermined angle. From this moment onwards, the force acting on the point of application is no longer determined by the direction between the point of application and the second bearing point of the elastic element, but rather by the direction between the point of application and the point at which the mounting element fits closely on the elastic element. If this point is located as close as possible to the rotational axis, preferably precisely on the rotational axis, the force that is applied by the part of the elastic element runs almost exactly or exactly axially, such that a torque is no longer exerted on the arm support element. This force can be adjusted by shifting or altering the position of the mounting element.

Therefore, it is preferable if the predetermined angle and/or the change in the force to be applied can be adjusted, preferably by ensuring that the mounting element can be shifted relative to the arm support element and/or the force transmission element. This may be achieved, for instance, by ensuring that the mounting element can be shifted in a slot and, for example, fixed by a screw. Alternatively or additionally, the mounting element may be designed to be an eccentric.

The invention solves the problem at hand by way of a device which is characterized by the fact that the arm support element is connected to the force transmission element via a joint. In a preferred configuration, in addition to a flexible arrangement of the force transmission element on the counter bearing, this is the only joint required to move the arm shell.

This joint is preferably configured and designed in such a way that, when the device is mounted, an abduction and/or adduction of the user's arm is enabled. This movement corresponds to a lateral raising or lowering of the arm in the frontal plane. This movement is not impaired by the device and especially not by the joint.

The joint and the counter bearing element are preferably arranged at a distance from one another by way of the force transmission element. When the device is mounted, the joint is preferably arranged in a shoulder region of the user, especially preferably at the height of or higher than the glenoid cavity. Additionally or alternatively, the counter bearing element is preferably arranged in a pelvic region of the user, preferably on the user's pelvis, more preferably still on or below the iliac crest and above the hip joint of the user. The positioning of the joint and the counter bearing element are deemed advantageous for all configurations described here.

In a favorable configuration, when the device is mounted, the counter bearing element is at a lateral offset to the spine of the user. This offset is preferably less than five centimeters when regarded from the center of the spine.

In a preferred configuration of the present invention, the device, which is provided with only one arm support element, is designed in such a way that it can be used to support both the right arm and the left arm. To this end, the force transmission element and, where applicable, the passive actuator can be released. This is particularly easy to achieve if the force transmission element is only inserted into a pocket of the counter bearing element, thereby rendering it easy to remove. All other components that are required to support the one arm are preferably arranged on the force transmission element. They are thus also removed from the counter bearing element. The force transmission element is then inserted into another pocket of the counter bearing element or fixed to another point of the counter bearing element, thereby enabling it to be used to support the other arm. To this end, the force transmission element and preferably all components that are fixed to it, both directly and indirectly, are designed to be symmetrical so as to enable its use for both a right and a left arm.

One end of the passive actuator is preferably arranged on the force transmission element or the counter bearing element, while the other end engages with a part of the arm support element, such as a force application lever that is arranged on said sup-6 port element. However, it is of course possible and beneficial for certain applications for one end of the passive actuator to engage with the arm support element and the other end with the force transmission lever, which is connected to the force transmission element such that it is torque-proof. In this case, the actuator is also configured to apply a supporting force to the arm support element.

BRIEF DESCRIPTION OF THE DRAWINGS

In the following, an example of an embodiment of the present invention will be explained in more detail by way of the attached drawings: They show.

DETAILED DESCRIPTION

Figure 1:
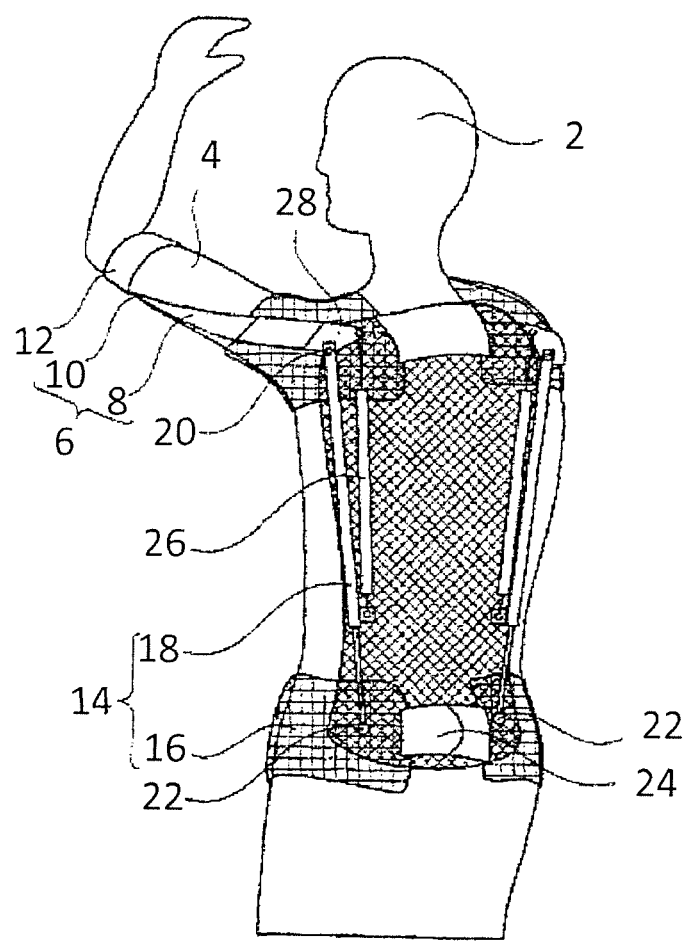
FIG. 1—a schematic depiction of a device according to a first example of an embodiment of the present invention when in the mounted state, FIGS. 2-6—a depiction of a mounted device in various positions from a lateral perspective, FIGS. 7-9—depictions of a mounted device in a top view from above, FIG. 10 a schematic depiction of a device according to a further example of an embodiment of the present invention, FIG. 11—a schematic depiction of a section of a device, FIGS. 12-15—schematic depictions of devices according to further examples of an embodiment of the present invention, FIGS. 16 and 17—exemplary depictions of force patterns, FIG. 18—a schematic view of a mounted device, FIGS. 19 and 20—schematic depictions of individual elements of the device, FIG. 21—various steps in releasing a strap, FIGS. 22 and 23—various forms of end stops, FIGS. 24 to 26—different ways to adjust an applied force and FIGS. 27 to 29—further examples of an embodiment of the invention.

FIG. 1 shows a user 2 wearing a device for supporting an arm 4. The device features an arm support element 6, which comprises a spacer element 8 and an arm shell 10. The arm support element 6 is arranged at its distal end via a sleeve 12 on the arm 4.

The device also features a counter bearing 14, which comprises a counter bearing element 16 and a force transmission element 18. The spacer element 8 of the arm support element 6 is arranged via a joint 20 to the upper end of the force transmission element 18 depicted in FIG. 1. This is designed in the form of a rod, for example. In the example of an embodiment depicted, the force transmission element 18 is a telescopic rod. In the example of an embodiment shown, the lower end of the force transmission element 18 is arranged on the counter bearing element 16 via a ball joint 22. The counter bearing element 16 serves to transmit the forces arising to a stable element. It may lie on a ground, an object or a body part. In the example of an embodiment depicted, the counter bearing element 16 is a hip strap that lies in the hip region of the user 2. The length of the counter bearing element 16 can be set by way of an adjustment device 24. On the one hand, this is convenient for the user 2 and on the other hand, it is practical for achieving as exact a positioning as possible of the ball joints 22 on the body of the user 2.

The device shown in FIG. 1 also has a passive actuator 26, which is designed in the form of a tension spring in the example of an embodiment shown. The lower end of the passive actuator 26 shown in the FIG. 1 is arranged on the force transmission element, whereas the opposite end engages with a lever element 28 of the spacer element 8 of the arm support element 6. A force is applied to the lever element 28, and thereby the spacer element 8 of the arm support element 6, by the passive actuator 26, said force counteracting the force of gravity and supporting the arm 4 of the user 2.

The device shown in FIG. 1 comprises two arm support elements 6, two counter bearings 14 and two passive actuators 26, only one of which has been described for the sake of clarity.

Figure 2:
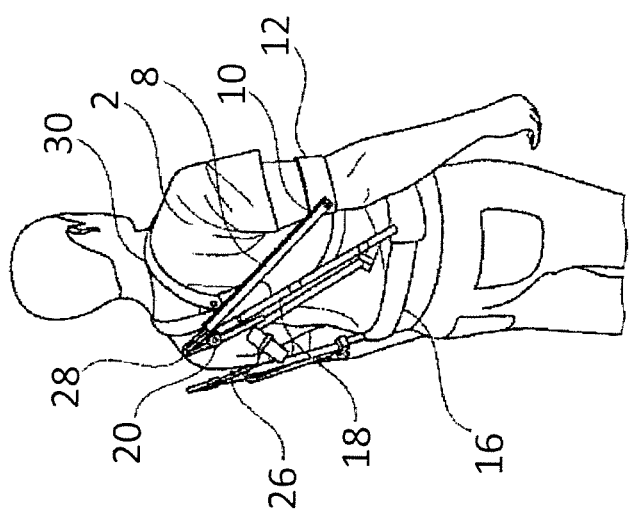

The FIGS. 2 to 6 depict a device according to an example of an embodiment of the present invention in a mounted state, wherein the user 2 has executed a range of movements. FIG. 2 shows the user 2 in a relaxed standing position, while in FIG. 3 the user 2 can be seen with spread arms. The respective arm shell 10 is attached to the arm via a sleeve 12 and, together with the spacer element 8, forms the arm support element 6. It is connected to the force transmission element 18 via the joint 20, wherein the respective force transmission elements 18 are arranged on the counter bearing element 16 in the form of a hip strap. The lever element 28, with which the passive actuator 26 engages, is situated on the joint 20.

Figure 3:
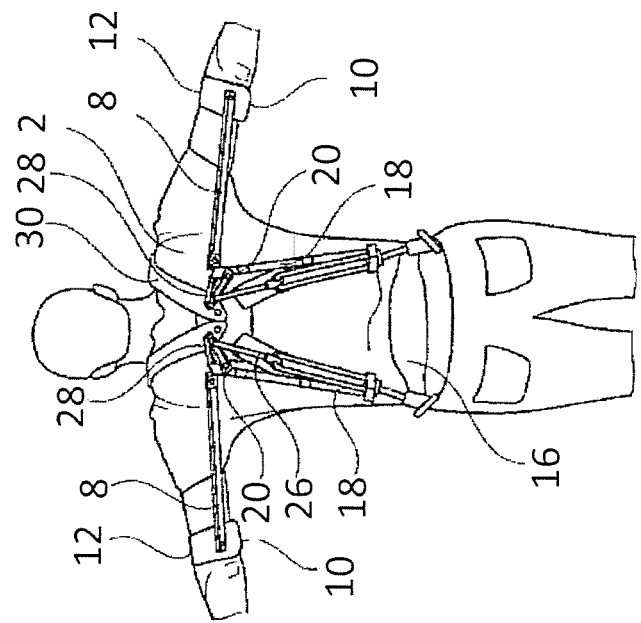

In FIG. 2, in a relaxed standing position, it is clear to see that the joint 20 moves backwards away from the user's 2 body. If the user 2 spreads his arms, as shown in FIG. 3, the respective joint 20 moves towards the body of the user 2. In the example of an embodiment depicted, the joint 20 is situated in the vicinity of the shoulder joint. The device also features two shoulder straps 30 which hold the device on the body. They do not serve to keep the joints 20 at a predetermined distance from the body.

Figure 5:
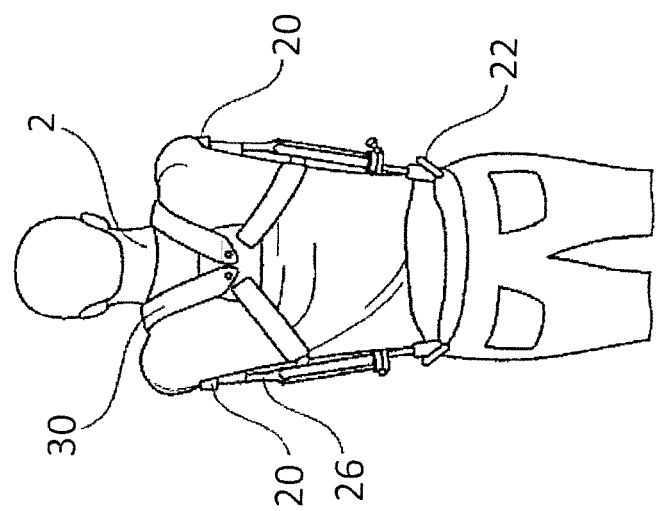
Figure 4:
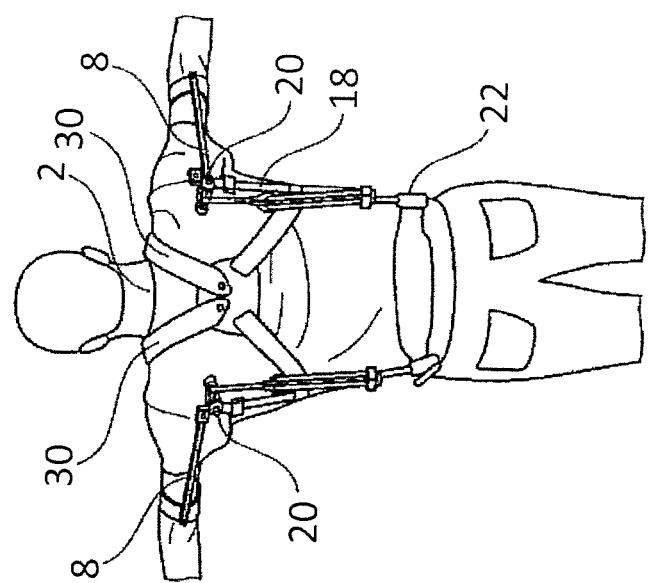

FIG. 4 shows a further raising of the arms in comparison to FIG. 3. The arms in FIGS. 4 and 5 are also moved further forwards by the user 2. It is clear that the two joints 20 move away from one another and in particular are not connected to the shoulder straps 30 in order to maintain a predetermined distance. Rather, the joints 20 and the force transmission elements 18 and the spacer elements 8, which are connected to one another via the joints 20, move outwards and can be moved almost completely freely. It is evident that the device can function without any complicated supplementary articulation mechanisms or rigid splint system. Whereas the joints 20 in FIGS. 3 and 4 are still behind the body of the user 2 in the shoulder blade region, in FIG. 5 they have moved to the sides of the user 2 simply as a result of the movement of the body and are therefore able to follow the movement. FIG. 6 shows the position depicted in FIG. 5 in a lateral view. The arms 4 of the user 2 cross over and, as depicted in FIG. 6, the joints 20 are situated next to the shoulder of the user 2. At the same time, the ball joints 22, by means of which the force transmission element 18 is arranged on the counter bearing element 16, have not changed. The position of these ball bearings 22 remains unchanged, regardless of any movement of the arms 4 of the user 4. Such a freedom of movement achieved with such low structural complexity is barely possible with devices known from the prior art.

FIGS. 7 to 9 show a top view of various positions of the user 2 and his arms 4. In FIG. 9, the arms are widely spread out and are moved forwards via the positions in FIGS. 7 and 8 until they cross, as shown in FIG. 8. It is clearly shown how the joints 20 move outwards from FIG. 9 via FIG. 7 to FIG. 8 and stay consistently very close to the body of the user 2 in the process.

Figure 10:
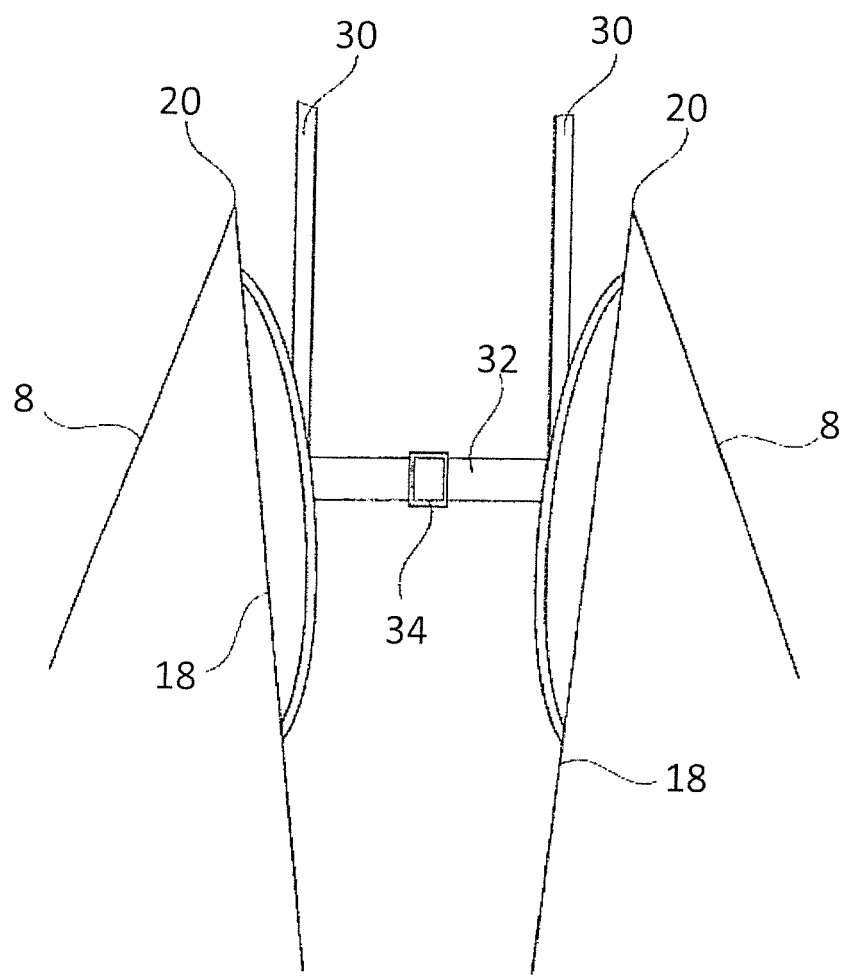

FIG. 10 shows the schematic depiction of a joint according to another example of an embodiment. The spacer elements 8 can be seen, which are connected to the force transmission elements 18 via joints 20. Unlike the examples of an embodiment depicted in FIGS. 2 to 9, there is now one connection element 32 between the two force transmission elements, said connection element being designed as an elastic strap in the example of an embodiment shown. The length of the strap can be adjusted by way of a clasp 34, such that the applicable tensile force is adjustable.

The two shoulder straps 30 are also depicted, by means of which the device 1 can be arranged on the body of the user 2. The counter bearing element is not shown. This is shown in FIG. 11. It comprises another strap 36, which features a padding 38 on the side facing the body so as to render the device as comfortable as possible to wear. The force transmission element 18 is inserted into a pocket 40 provided specifically for this purpose and can be swivelled inside said pocket, thereby performing the function of a ball joint. The particularly simple structure that this entails means that complicated joint arrangements can be avoided.

FIG. 12 shows the schematic depiction wherein the device has been integrated into an item of clothing, in this case a t-shirt. The counter bearing element 16 now consists of two shoulder elements that are connected to the spacer elements 8 and the arm shells 10 via the force transmission elements 18 and corresponding joints 20. The fact that the device is integrated into a t-shirt renders it especially easy to mount and remove, thereby eliminating the need for complicated movements. This increases the acceptance of the device.

FIG. 13 depicts an exoskeleton with various splints and joints, by means of which a force from a hip element 44 can be introduced into ground contact elements 46 that are specifically provided for this purpose.

Figure 14:
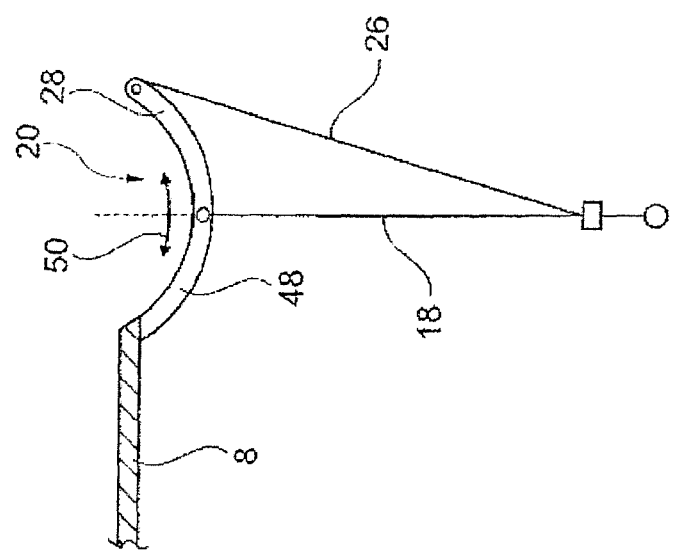

FIG. 14 shows the schematic depiction according to another configuration of the joint 20. A pivot lever 48 connects the spacer element 8 and the force transmission element 18, the upper end of which in FIG. 14 is moveably arranged in an elongated hole, not depicted, or a slot. During swivelling, the articulation point of the force transmission element 18 on the pivot lever 48 now shifts in the direction of the double arrow 50. This results in a change in the length of the lever element 28 and hence also in the force applied by the passive actuator 26.

Figure 15:
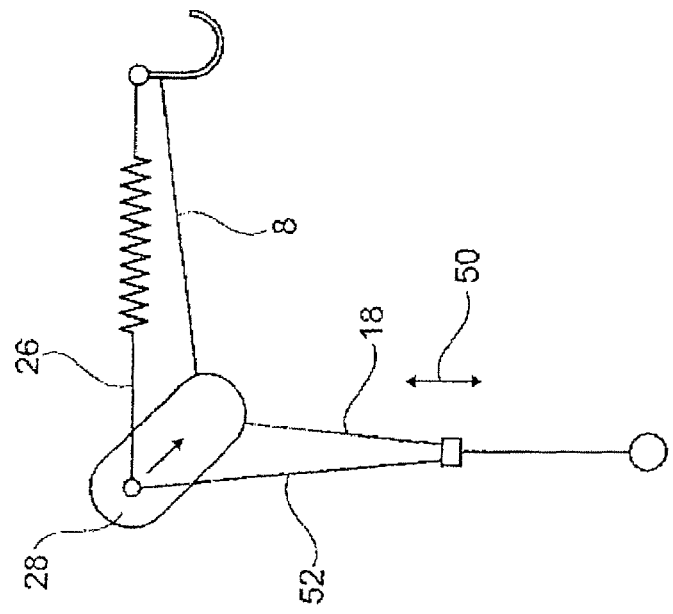

FIG. 15 depicts a further configuration wherein, unlike with the previous configurations, the passive actuator 26 is not arranged between the lever element 28 and the force transmission element 18, but rather between the lever element 28 and the distance element 8. A preload is applied to the passive actuator 26 via a counter tensioner 52, whose position on the force transmission element 18 can be shifted along the double arrow 50.

Figure 16:
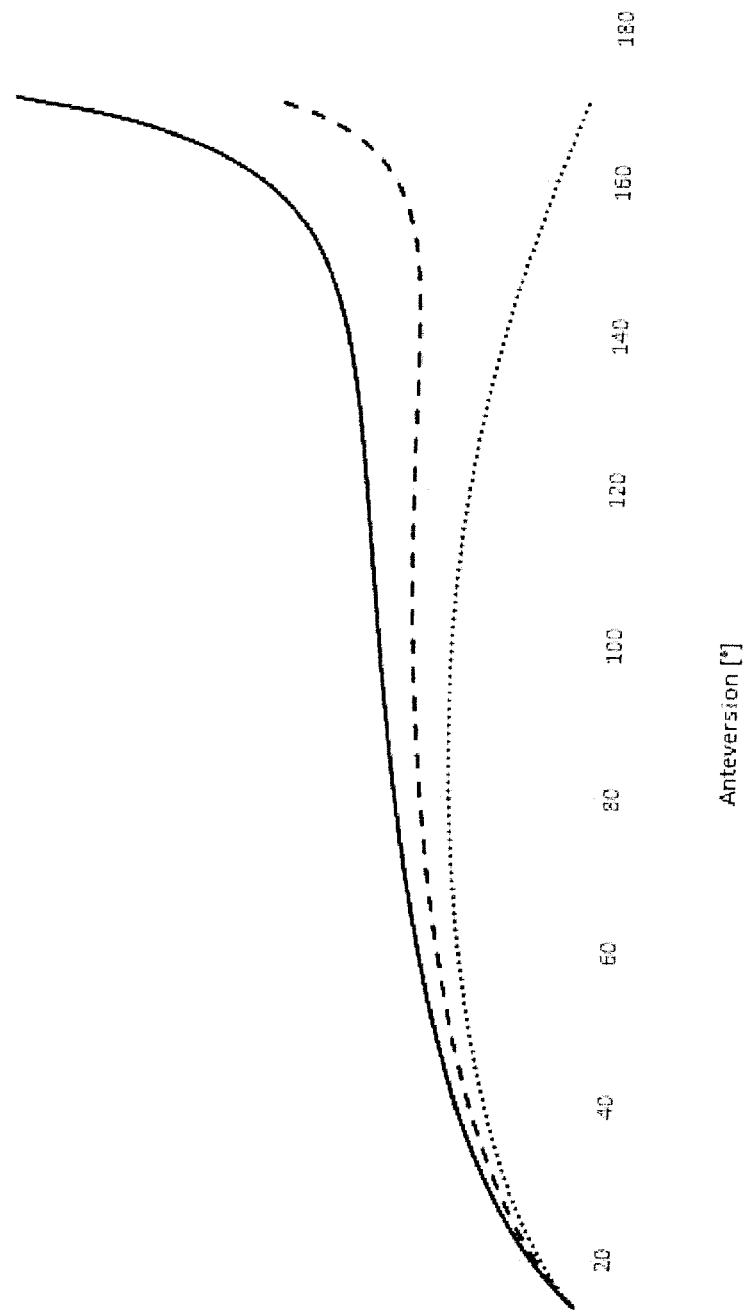
Figure 17:
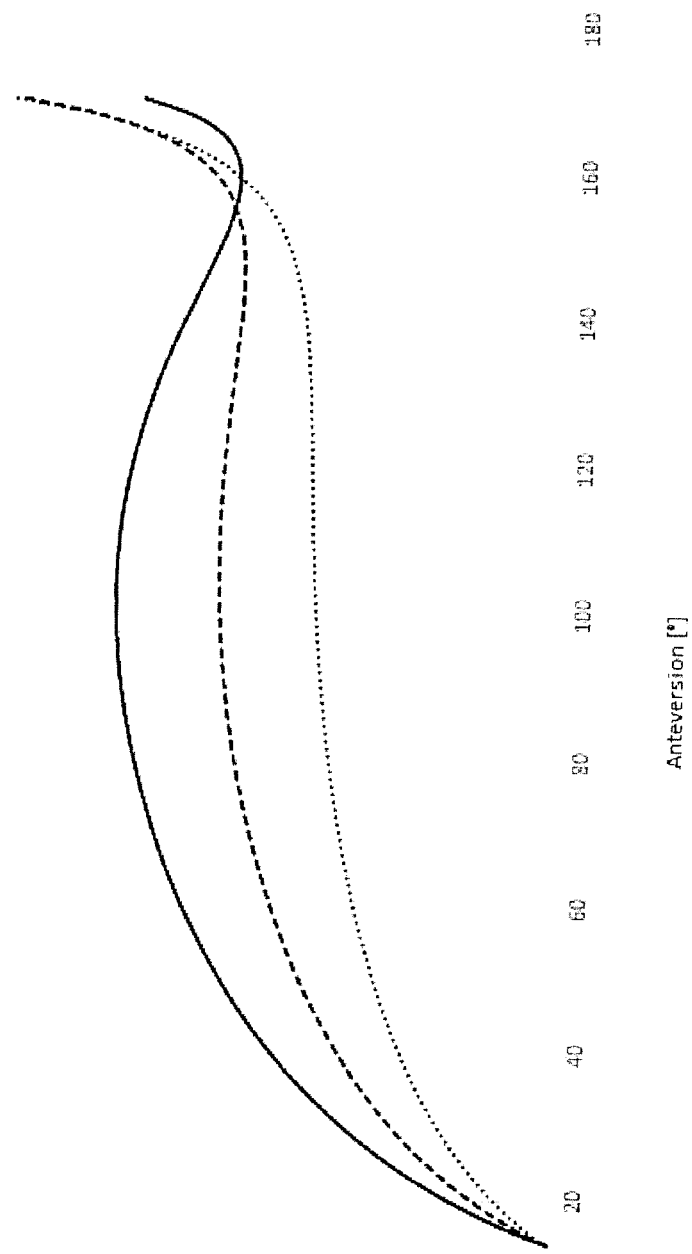

The FIGS. 16 and 17 show various force patterns that may be applied to the arm by the device according to examples of an embodiment of the present invention. An anteversion angle is plotted on the X axis. The anteversion is the raising of the arm in a sagittal plane, i.e. forwards in the present example. 0° corresponds to the loosely hanging arm. FIG. 16 shows that a force is not applied until a predetermined angle has been reached. A torque ratio is plotted on the Y axis. The torque generated by the net weight of the arm and the force of gravity has been divided by the torque effected by the device.

The various force patterns can be adjusted on an almost individual basis and, in the example of an embodiment shown, generated by a single passive actuator 26 that is pretensioned to varying degrees. While the dotted line has been generated by a passive actuator 26 which features almost no preload, the preload increases across the dashed line and the solid line.

FIG. 17 also depicts the force that can be applied to the arm via the angle of an anteversion, yet wherein the preload of the actuator now remains unchanged. Instead, an articulation point is shifted via which the passive actuator 26 transfers its force to the support element 6. In this case, the distance of the force articulation point from the torque of the joint 20 increases from the dotted line, via the dashed line to finally reach the solid line. It is clear that, as a result, it is possible to achieve an increase in force across a broad angular range, in particular at big angles from approx. 150° upwards; however, this results in the emergence of a considerably different pattern to be patterns shown in FIG. 16.

Figure 18:
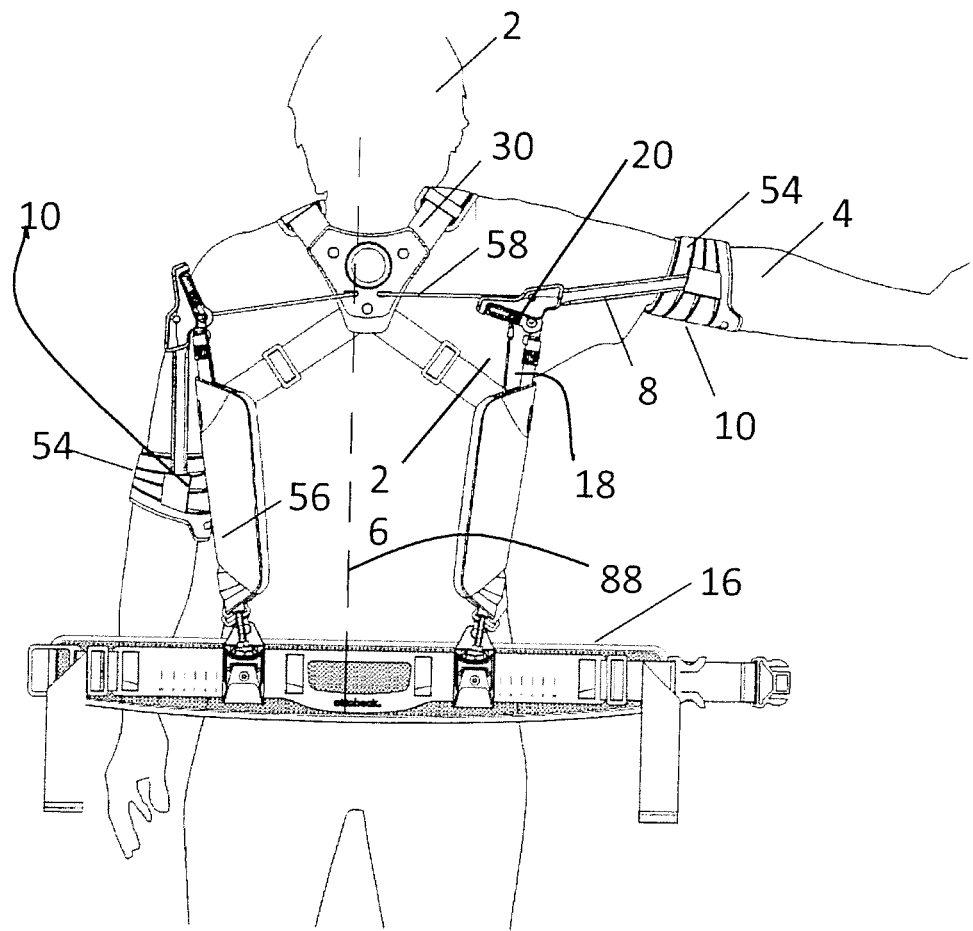

FIG. 18 shows the device in its almost mounted state. The counter bearing element 16 in the form of a hip strap is still open, whereas the arm shells 10 have already been closed around the arm 4 of the user by way of a fastening element 54. The spacer elements 8 are arranged on the respective force transmission element 18 via a joint 20, wherein the force transmission element is arranged in a cladding 56. The passive actuator 26 is designed in the form of an elastic cable or wire. A tension element 58 is arranged on the spacer elements 8, said tension element connecting the two spacer elements 8 and thus the two arm support elements 6 to one another. The device also features shoulder straps 30 through whose connection element the tension element 58 is guided.

In FIG. 18, the center of the spine 88 is also depicted. It corresponds to an imagined symmetrical axis of the spine. It is clear to see that the lower ends of the force transmission elements 18, which are connected to the counter bearing elements 16 or arranged inside them, are spaced laterally from the spinal axis 88. Inevitably, this also applies for the counter bearing elements 16 themselves.

Figure 19:
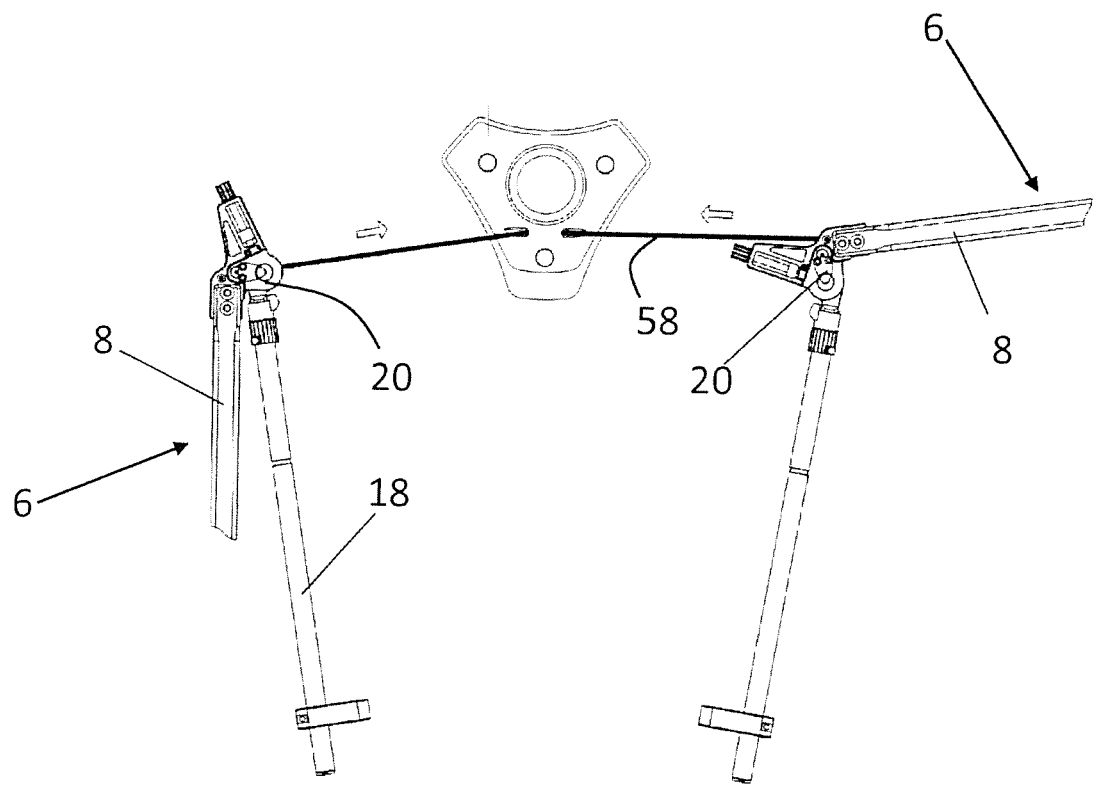

Elements of this configuration are shown in FIG. 19. On the two force transmission elements 18, one spacer element 8 of one arm support element 6 is arranged such that it can swivelled about one joint 20. The tension element 58 is situated between the two spacer elements 8, wherein the tension element runs through the connection element between the shoulder straps, which are not depicted.

Figure 20:
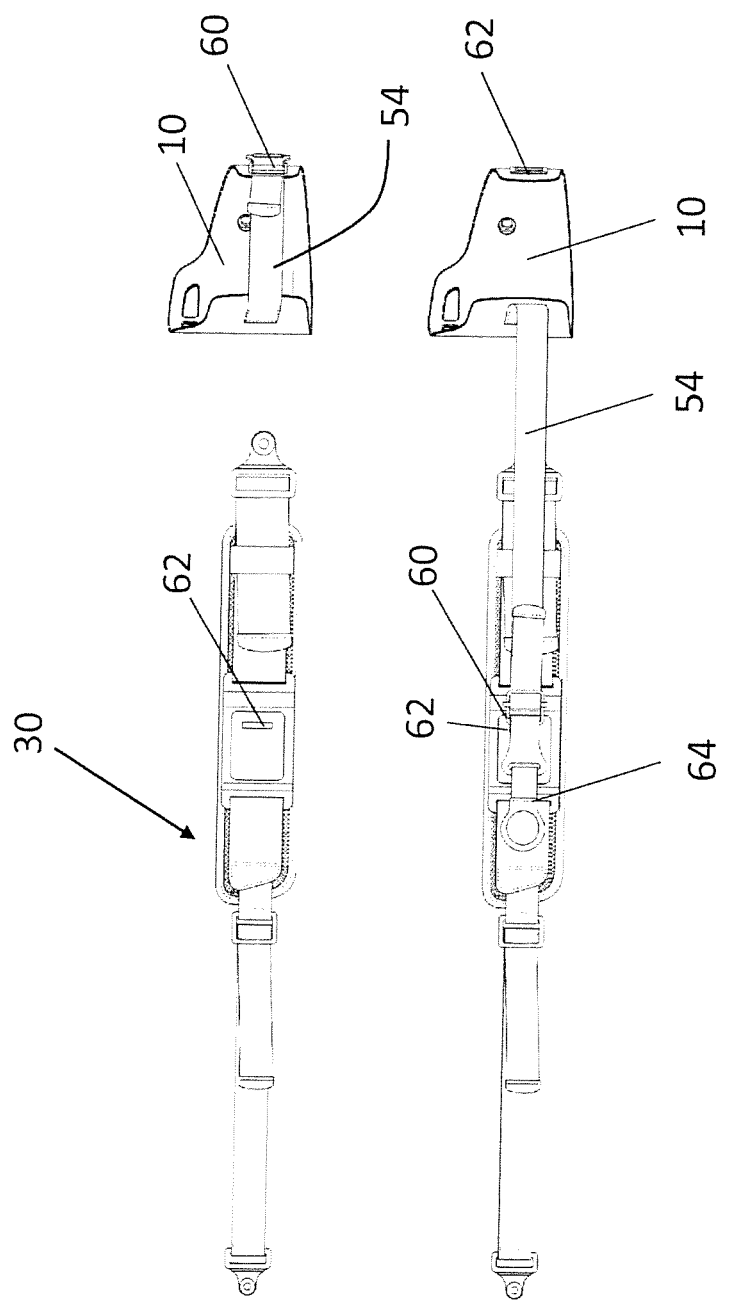

The upper part of FIG. 20 depicts one of the shoulder straps 30, as well as an arm shell 10 with a fastening element 54 arranged on it. The fastening element 54 has a fixing element 60 in the form of a clasp which can engage with a loop 62 depicted in the lower part of FIG. 20 in order to close the arm shell 10 around an arm, which is not depicted. The shoulder strap 30 has a comparably designed loop 62. The fastening element 54 in an open state is depicted in the lower part of FIG. 20. The arm shell 10 no longer completely encloses the arm. The fixing element 60 is now inserted in the loop 62 of the shoulder strap 30 and can thus be stored securely. A grip element 64 is situated at the end of the fastening element 54, by means of which the fastening element 54 can be easily held.

Figure 21:
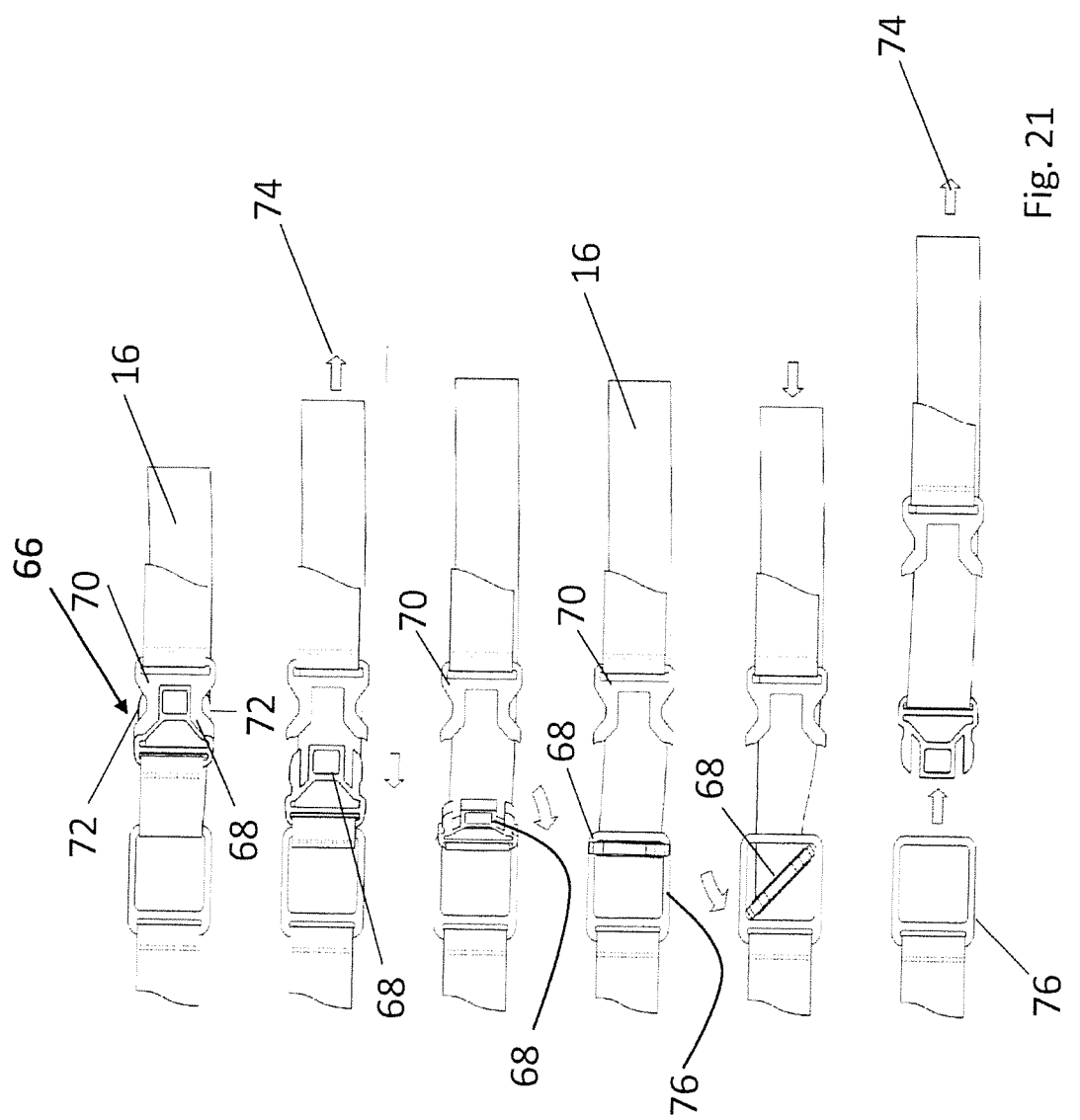

FIG. 21 shows the various phases in the opening of a fastener 66 of the counter bearing element 16, which is preferably designed as a hip strap. Such a strap is also practical for other objects and is an invention in its own right, either as a stand-alone invention or as part of a device, especially an orthosis or prosthesis. The uppermost image depicts the fastener 66 in a closed state. It comprises a clasp, whose ratchet element 68 engages by way of positive-locking with a ratchet accommodation 70 specifically provided for this purpose. By pressing the two activation elements 72 together, the ratchet element 68 and the ratchet accommodation 70 can be separated, as shown in the second image from the top. A tensile force is exerted along the arrow 74. The third image from the top shows that this tensile force effects a tilting of the ratchet element 68 until it is in an almost vertical position in relation to the drawing plane, as shown in the fourth image from the top. A further separation of the two ends of the counter bearing element 16 is not possible as the ratchet element 68 does not pass through the loop 76 in this position. For this to happen, the ratchet element 68 must first of all be tilted, as shown in the second image from the bottom. It is only when it has reached this position that it passes through the loop 76 and the two elements can be separated from one another if a force is exerted along the arrow 74, as shown in the bottom-most image. This results in a safety mechanism being inserted into the fastener 66 that prevents a full release and thus a snapping or striking back of the individual ends of the counter bearing element 16 by a mere activation of the activation elements 72.

Figure 22:
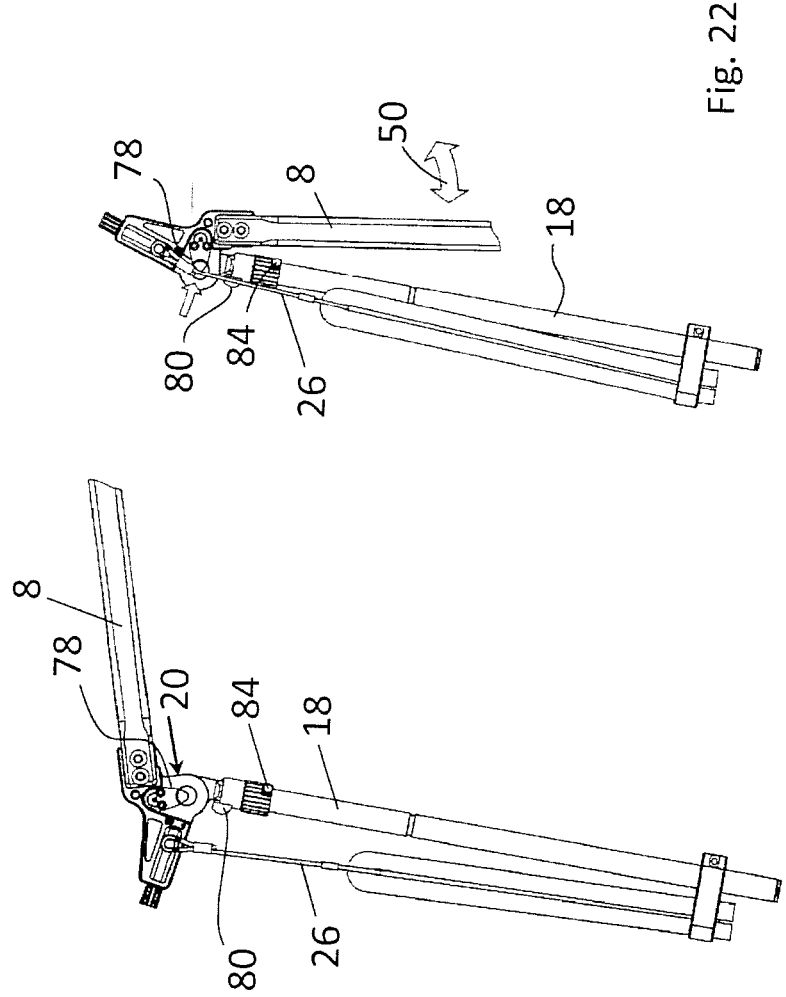

The left-hand image of FIG. 22 once again depicts the force transmission element 18, the spacer element 8 and the passive actuator 26. A mounting element 78 is also provided in the joint 20 region: In the left-hand image of FIG. 22, said mounting element is not yet lying on the elastic element, which acts as a passive actuator. This is different in the right-hand image of FIG. 22. It is clear to see that the mounting element 78 is lying on the elastic element, which acts as a passive actuator. Given that the mounting element 78 is preferably situated precisely on the rotational axis of the joint 20, the contact between the elastic element and the mounting element 78 prevents the elastic element from applying a force to the arm support element 6, which effects a torque on the arm support element 6. The elastic element is divided into two parts by the close-fitting mounting element 78, wherein each of these parts is able to exert a force but not to generate a torque, since the forces are directed radially towards the rotational axis of the joint 20. The angle between the arm support element 6 and the force transmission element 18, at which the mounting element 78 lies on the elastic element, is preferably adjustable. A further swivelling of the arm supprt port 6 in a clockwise direction then occurs without a force being applied to the arm support element 6 by the elastic element, i.e. the passive actuator.

FIG. 23 shows the situation in the left-hand image. The end stop 80 would prevent a further swivelling of the spacer element 8 about the joint 20 relative to the force transmission element 18. If the device is to be stowed away, for example, or the projection 80 brought into the passive position, the projection 80 is disengaged from the spacer element 8 along the arrow 74, as shown in the second image from the left. As shown in the second image from the right, the spacer element 8 can now be freely swivelled in both directions along the double arrow 50 in relation to the force transmission element 18 and thus brought into the position depicted on the far right.

FIG. 24 shows a possible way of generating an adjustable force that is applied by the passive actuator 26. At a point of application 82, which is arranged eccentrically in relation to the joint 20, the passive actuator engages with the spacer element 8 of the arm support element 6. By using a suitable tool, a screwdriver in the example of an embodiment shown, the position of the point of application 82 relative to the swivel axis of the joint 20 can be adjusted via a positive-locking element and the eccentricity thus set and the force applied by the passive actuator 26 modified. An alternative or additional possibility is depicted in FIG. 25. Both diagrams in this figure shows a force transmission element 18 and a spacer element 8 that is arranged on it. In contrast to the diagram shown in FIG. 24, the diagram is rotated by 90°. They each have two passive actuators 26 which engage with the point of application 82 on the spacer element 8 that lies opposite. If the force is now to be adjusted, alternatively or additionally to the measure shown in FIG. 24, one or both of the passive actuators 26 can be removed and replaced by another. This also enables an adjustment of the force. Should the passive actuator 26 remain in place, so it can be used at a later point in time for example, its upper fixing loop can be arranged on the projection 84.

FIG. 26 shows the joint 20 with the spacer element 8 of the arm support element 6 and the force transmission element 18. It is clear that the application point 82 is designed to be moveable. To this end, the device has a motor 86, by means of which the gear wheels shown in the left-hand part of FIG. 26 can be driven, which causes the application point 82 to be moved. The motor can be used to bring the system into a state of minimal force, thereby almost fully—preferably fully—deactivating it, which is especially beneficial when mounting and removing the device or when the support is not necessary for other reasons.

FIGS. 27 and 28 correspond to the depiction in FIG. 18, the difference being that two further tension elements 58 are provided that are not arranged between the arm supports 6; rather, each tension element is arranged between one of the arm supports 6 and the counter bearing element 16. These also serve to hold the arm shells 10 on the arm. Furthermore, the elements for the two arms are independent of one another, such that any interference is prevented. In FIG. 28, the tension element 58 shown in FIG. 18 has also been removed.

FIG. 29 shows an embodiment of the present invention wherein, unlike with the other embodiments depicted, the passive actuator 26 is not arranged between a force application lever of the arm support element 6 and the force transmission element 18 or the counter bearing element 16; rather, it extends between a force application lever of the force transmission element 18 and the arm support element 6. This also allows for a supporting force to be exerted on the arm support element 6.

REFERENCE LIST 2 user
4 arm
6 arm support element
8 spacer element
10 arm shell
12 sleeve
14 counter bearing
16 counter bearing element
17 mounting element
18 force transmission element
20 joint
22 ball joint
24 adjustment device
26 passive actuator
28 lever element
30 shoulder strap
32 connecting element
34 clasp
36 strap
38 adding
40 pocket
42 exoskeleton
44 hip element
46 ground contact element
48 pivot lever
50 double arrow
52 counter tensioner
54 fastening element
56 cladding
58 tension element
60 fixing element
62 loop
64 grip element
66 fastener
68 ratchet element
70 ratchet accommodation
72 activation element
74 arrow
76 loop
78 mounting element
80 projection
82 point of application
84 projection
86 motor
88 spinal axis

The invention claimed is:

1. A device for supporting at least one arm of a user, comprising:
   at least one arm support element with an arm shell for placing the at least one arm of the user on the arm shell;
   at least one passive actuator which is configured to apply a force to the at least one support element;
   at least one counter bearing for the force to be applied by the at least one passive actuator which comprises
      at least one counter bearing element, and
      at least one force transmission element that is configured to transmit a counter force to the at least one counter bearing element; and
   at least one joint between the at least one arm support element and the at least one force transmission element,
   wherein the at least one joint is located in a shoulder blade region of the user when the device is in a mounted state,
   wherein the at least one force transmission element extends between the at least one counter bearing element and the at least one arm support element,
   wherein the at least one counter bearing element is positionable at a hip of the user and mountable on the hip of the user, and
   wherein the device is configured such that a freedom of movement of the spine of the user is not restricted.

2. The device according to claim 1 wherein the at least one force transmission element is a compressive force transmission element to which the at least one arm support element is arranged such that the at least one arm support element is swivellable about a swivel axis.

3. The device according to claim 2, wherein the at least one joint connects the at least one arm support element to the at least one force transmission element.

4. The device according to claim 2 wherein the compressive force transmission element is connected to the at least one counter bearing element by a joint.

5. The device according to claim 1 wherein the at least one force transmission element has a changeable orientation relative to the at least one counter bearing element by way of a movement of the torso of the user and/or a movement of the arm of the user.

6. The device according to claim 1 wherein the at least one passive actuator has at least one elastic element.

7. The device according to claim 1 wherein the at least one passive actuator is configured to apply the force depending on a position and/or orientation of the at least one arm support element relative to the at least one counter bearing element.

8. The device of claim 7 wherein the at least one passive actuator is configured to apply the force to the at least one arm support element eccentrically.

9. The device of claim 7 wherein the at least one passive actuator is configured to apply the force to the at least one arm support element depending on a swivel angle of the at least one arm support element about a swivel axis.

10. The device according to claim 1 wherein the at least one passive actuator is configured to apply the force in a way which is alterable by a preload of the at least one passive actuator.

11. The device according to claim 1 wherein the at least one force transmission element is mounted in a guide which prevents a part of the at least one force transmission element on which the at least one arm support element is arranged from moving away from the torso of the user when the device is mounted on the user.

12. The device according to claim 1 wherein the at least one support element includes two arm support elements for supporting both arms of the user, wherein the at least one force transmission element includes two separate force transmission elements, and wherein each of the two arm support elements is arranged on a separate force transmission element such that it can be swiveled, and at least one connecting element is arranged between the separate force transmission elements so that a tensile force can be applied to the two force transmission elements, wherein both force transmission elements are connected to the at least one counter bearing element at a same point.

13. The device according to claim 1 further comprising a blocking device for blocking a movement of the at least one arm support element relative to the at least one force transmission element in at least one direction.

14. The device according to claim 13 wherein the movement is blockable completely.

15. The device of claim 1 configured so as to permit inclination by a user and/or a freedom of movement of the arm.

16. The device according to claim 1 wherein the at least one force transmission element includes two separate force transmission elements moveable independently from one another.

17. The device according to claim 1 wherein a strength of the force that is applied by the at least one passive actuator is adjustable by adjusting a point of application of the force at the at least one joint between the at least one arm support and the at least one force transmission element.

18. The device according to claim 1, wherein the at least one joint is moveable away from a body of the user when the at least one arm is moved.

19. The device according to claim 1 further comprising at least one joint on the at least one counter bearing element, wherein the at least one force transmission element is connected to the at least one counter bearing element by the at least one joint, and wherein the at least one joint is moveable relative to the at least one counter bearing element.

20. The device according to claim 1 wherein the at least one passive actuator has a lower end associated with the at least one force transmission element and an upper end that is configured for applying the force to the at least one arm support element.

21. The device for supporting at least one arm of a user, comprising:
   at least one arm support element with an arm shell for placing the at least one arm of the user on the arm shell;
   at least one passive actuator which is configured to apply a force to the at least one support element;
   at least one counter bearing for the force to be applied by the at least one passive actuator which comprises
      at least one counter bearing element, and
      at least one force transmission element that is configured to transmit a counter force to the at least one counter bearing element, wherein the at least one force transmission element is a compressive force transmission element to which the at least one arm support element is arranged such that it is swivellable about a swivel axis; and
   a joint for connecting the at least one arm support element to the force transmission element,
   wherein the at least one force transmission element extends between the at least one counter bearing element and the at least one arm support element,
   wherein the at least one counter bearing element is positionable at a hip of the user and mountable on the hip of the user,
   wherein the at least one arm shell is movable in at least three translational and three rotational degrees of freedom in relation to the at least one counter bearing element, and
   wherein the device is configured such that when the device is mounted on the user, the joint is located in a shoulder blade region of the user.

22. The device according to claim 21 wherein the compressive force transmission element is connected to the at least one counter bearing element by a joint.

23. The device according to claim 21 wherein the at least one passive actuator has at least one elastic element.

24. The device according to claim 21 wherein the at least one passive actuator is configured to apply the force depending on a position and/or orientation of the at least one arm support element relative to the at least one counter bearing element.

25. The device according to claim 21 wherein the at least one passive actuator is configured to apply the force in a way which is alterable by a preload of the at least one passive actuator.

26. The device according to claim 21 further comprising a blocking device for blocking a movement of the at least one arm support element relative to the at least one force transmission element in at least one direction.

27. The device according to claim 21 further comprising at least one joint on the at least one counter bearing element, wherein the at least one force transmission element is connected to the at least one counter bearing element by the at least one joint, and wherein the at least one joint is moveable relative to the at least one counter bearing element.

28. The device according to claim 21 wherein the at least one passive actuator has a lower end associated with the at least one force transmission element and an upper end that is configured for applying the force to the at least one arm support element.

29. The device for supporting at least one arm of a user, comprising:
   at least one arm support element with an arm shell for placing the at least one arm of the user on the arm shell;
   at least one passive actuator which is configured to apply a force to the at least one support element;
   at least one counter bearing for the force to be applied by the at least one passive actuator which comprises
      at least one counter bearing element, and
      at least one force transmission element that is configured to transmit a counter force to the at least one counter bearing element, wherein the at least one force transmission element is connected to the at least one counter bearing element and is moveable about a point of connection to the at least one counter bearing element,
   wherein the at least one arm support element is connected to the at least one force transmission element via a joint,
   wherein the joint is moveable together with movements of the at least one force transmission element about the point of connection to the at least one counter bearing element, and is configured to allow for an abduction and/or adduction of the arm of the user when the device is mounted on the user, and
   wherein the joint and the at least one counter bearing element are arranged a distance from one another by way of the at least one force transmission element, wherein the joint is arranged in a shoulder region of the user when the device is mounted on the user, and the at least one counter bearing element is arranged in a pelvic region of the user.

30. The device according to claim 29 wherein the at least one counter bearing element is arranged at a lateral offset to the spine of the user when the device is mounted on the user.

31. The device according to claim 29 wherein the at least one passive actuator has a first end arranged on the at least one force transmission element or the at least one counter bearing element, and a second end that lies opposite to the first end wherein the second end is arranged on the at least one arm support element, or the first end is arranged on the at least one arm support element and the second end on the at least one force transmission element.

32. The device according to claim 29 wherein the shoulder region of the user is at a height of or higher than a glenoid region of the user, and wherein the pelvic region is on or below an iliac crest and above a hip joint of the user.

33. The device according to claim 29 wherein the point of connection to the at least one counter bearing element comprises a ball joint.

34. The device for supporting at least one arm of a user, comprising:
- at least one arm support element with an arm shell for placing the at least one arm of the user on the arm shell;
- at least one passive actuator which is configured to apply a force to the at least one support element;
- at least one counter bearing for the force to be applied by the at least one passive actuator which comprises
  - at least one counter bearing element, and
  - at least one force transmission element that is configured to transmit a counter force to the at least one counter bearing element, wherein the at least one force transmission element is connected to the at least one counter bearing element and is moveable about a point of connection to the at least one counter bearing element,
- wherein the at least one arm support element is connected to the at least one force transmission element via a joint,
- wherein the joint is moveable together with movements of the at least one force transmission element about the point of connection to the at least one counter bearing element, and is configured to allow for an abduction and/or adduction of the arm of the user when the device is mounted on the user,
- wherein the at least one passive actuator has a first end arranged on the at least one force transmission element or the at least one counter bearing element, and a second end that lies opposite to the first end wherein the second end is arranged on the at least one arm support element, or the first end is arranged on the at least one arm support element and the second end on the at least one force transmission element, and
- wherein the at least one force transmission element comprises a force application lever, and wherein the second end of the at least one passive actuator is arranged on the force application lever.

* * * * *